United States Patent
Zhang

(10) Patent No.: US 10,919,889 B2
(45) Date of Patent: Feb. 16, 2021

(54) CHIRAL HETEROCYCLIC COMPOUND WITH HEDGEHOG PATHWAY ANTAGONIST ACTIVITY, METHOD AND USE THEREOF

(71) Applicant: SUZHOU KINTOR PHARMACEUTICALS, INC., Jiangsu (CN)

(72) Inventor: Xiaohu Zhang, Suzhou (CN)

(73) Assignee: SUZHOU KINTOR PHARMACEUTICALS, INC., Jiangsu (CN)

( * ) Notice: Subject to any disclaimer, the term of this patent is extended or adjusted under 35 U.S.C. 154(b) by 0 days.

(21) Appl. No.: 16/313,090

(22) PCT Filed: Jun. 30, 2017

(86) PCT No.: PCT/CN2017/091130
§ 371 (c)(1),
(2) Date: Dec. 24, 2018

(87) PCT Pub. No.: WO2018/006756
PCT Pub. Date: Jan. 11, 2018

(65) Prior Publication Data
US 2019/0161486 A1 May 30, 2019

(30) Foreign Application Priority Data
Jul. 4, 2016 (CN) .......................... 2016 1 0511917

(51) Int. Cl.
| | |
|---|---|
| *C07D 471/04* | (2006.01) |
| *A61P 35/00* | (2006.01) |
| *A61K 31/519* | (2006.01) |
| *A61K 31/517* | (2006.01) |
| *A61K 31/4745* | (2006.01) |
| *A61K 31/5377* | (2006.01) |
| *A61K 33/24* | (2019.01) |
| *A61K 31/506* | (2006.01) |
| *A61K 31/337* | (2006.01) |
| *A61K 45/06* | (2006.01) |

(52) U.S. Cl.
CPC .......... *C07D 471/04* (2013.01); *A61K 31/337* (2013.01); *A61K 31/4745* (2013.01); *A61K 31/506* (2013.01); *A61K 31/517* (2013.01); *A61K 31/519* (2013.01); *A61K 31/5377* (2013.01); *A61K 33/24* (2013.01); *A61K 45/06* (2013.01); *A61P 35/00* (2018.01)

(58) Field of Classification Search
CPC .................................................. C07D 471/04
See application file for complete search history.

(56) References Cited

FOREIGN PATENT DOCUMENTS

| CN | 103588771 | 2/2014 |
| WO | WO 2014/113191 | 7/2014 |

OTHER PUBLICATIONS

Nguyen et al. (Chiral Drugs: An Overview, International Journal of Biomedical Science, 2006, 2(2), pp. 85-100).*
Gulamhussen et al., "Highly efficient preparation of R-1-methyl-tetrahydroisoquinoline using chiral Ru(II)-catalyst," *Reaction Kinetics and Catalysis Letters*, 2(97):335-340, 2009.
PCT International Search Report and Written Opinion issued in International Application No. PCT/CN2017/091130, dated Sep. 6, 2017.

* cited by examiner

*Primary Examiner* — Susanna Moore
(74) *Attorney, Agent, or Firm* — Parker Highlander PLLC

(57) ABSTRACT

A chiral heterocyclic compound with hedgehog pathway antagonist activity, method and use thereof are provided. The chiral heterocyclic compound with hedgehog pathway antagonist activity has the structure represented by formula I. A pharmaceutical composition and combined application composition are also provided. Novel molecules of formula II that inhibit hedgehog pathway signaling and therapeutic applications for the treatment of malignancies, prevention of tumor regrowth, sensitization of radio-chemo therapies, and other diseases related to hedgehog signaling are also provided.

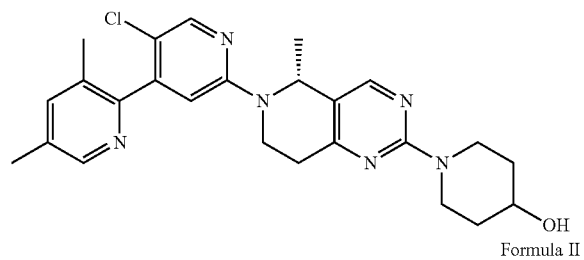

Formula I

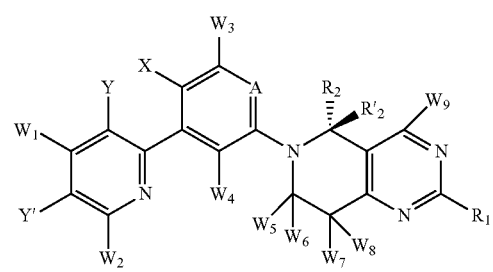

Formula II

18 Claims, 9 Drawing Sheets

CHIRAL HETEROCYCLIC COMPOUND WITH HEDGEHOG PATHWAY ANTAGONIST ACTIVITY, METHOD AND USE THEREOF

CROSS-REFERENCE TO RELATED APPLICATION

This is a US National Phase application based upon PCT Application No. PCT/CN2017/091130, filed Jun. 30, 2017 and titled "CHIRAL HETEROCYCLIC COMPOUND WITH HEDGEHOG PATHWAY ANTAGONIST ACTIVITY, METHOD AND USE THEREOF", which claims priority to Chinese patent application No. CN201610511917.7, filed Jul. 4, 2016, each of which is hereby incorporated by reference in its entirety.

FIELD

The present invention relates to the field of a chiral heterocyclic compound with Hedgehog pathway antagonist activity and its preparation method and use thereof, belonging to the field of medicinal technology. More particularly, the present invention relates to novel heterocyclic compounds that are useful in the field of cell signaling and treatment of cancer. More particularly, the present invention relates to therapies targeting the hedgehog signaling pathway mediated diseases, such as cancer, in mammals.

BACKGROUND

Malignant tumor is one of the major diseases that endanger human health. About 10.9 million new cases of malignant tumors occur each year, and about 6.7 million patients die each year due to malignant tumors[1]. Therefore, the prevention and treatment of tumor is also an important issue in the pharmaceutical industry, and anti-tumor drugs research and development has also undergone tremendous changes after years of research and exploration. Anti-tumor drugs previously used in clinical treatment are mainly cytotoxic drugs which have poor selectivity, strong side effects, easy to produce drug resistance and other shortcomings. In recent years, with the rapid progress of life science research, signal transduction in malignant tumor cells, cell cycle regulation, induction of apoptosis, angiogenesis and the interaction between cells and extracellular matrix and other basic processes are gradually elucidated. Therefore, some of the key enzymes of cell signal transduction pathways associated with tumor cell differentiation and proliferation are used as drug screening targets. New lead compounds, which selectively act on these specific targets, and with high efficiency and low toxicity properties, have become an important direction of tumor drug research and development. The market successes of targeted drugs such as trastuzumab, imatinib, gefitinib and erlotinib are typical examples[2].

Metastasis and regeneration are not only the characteristics of malignant tumors, but also a hurdle to treat malignant tumors. Even a new generation of targeted drugs has little effect on tumor metastasis and regeneration. Accordingly, in recent years, research on Hedgehog (Hh) signaling pathway—Hedgehog pathway by the scientific community has drawn more and more attentions. This is not only due to the abnormal activation of Hh signaling pathways that plays a pivotal role in the occurrence and development of many tumors, including basal cell carcinoma, brain tumors, breast cancer, prostate cancer and some digestive malignancies[3-11], but more importantly, because Hh signaling pathway is an embryonic development pathway, which plays an important role in the regulation of tumor stem cells, thus controlling tumor metastasis and regeneration.

The Hedgehog signaling pathway is a highly conserved intercellular signal transduction system. In 1980 it was named Hedgehog (Hh) pathway because in the fruit fly the gene mutation in this pathway can lead to larvae showing a number of hedgehog-shaped spurs[12]. Hh signaling pathway comprises of Hh ligand, two transmembrane protein receptors-patched membrane receptor (PTCH) and smoothened transmembrane protein (SMO), downstream transcription factor Gli protein and others[13]. PTCH and SMO are two transmembrane proteins located on the target cell membrane. PTCH is a cell surface receptor which is a 12 transmembrane protein encoded by the tumor suppressor gene PTCH, having a dual role of isolation and transduction Hh. SMO is a 7 transmembrane protein that is structurally highly similar to that of G protein-coupled receptor family and has the effect of transducing Hh signaling. PTCH and SMO act as receptors in the Hh signaling transduction process. Wherein PTCH is the receptor for Hh. When Hh is absent, PTCH prevents the translocation of SMO into the cell membrane, thereby inhibiting the activity of SMO, thereby inhibiting the transcriptional expression of the downstream genes. When the Hh signal is present, Hh binds to PTCH and induces phosphorylation of multiple serine/threonine residues at the C-terminus of SMO, resulting in the aggregation and activation of SMO on the cell surface; the activated SMO interacts with the kinesin-like molecule Costal2 (Cos2) and serine/threonine kinase fused (Fus), Suppressor offused (Sufu) to form a complex and dissociate from the microtubules. SMO plays a role in transcriptional activation by a full-length form, and ultimately leads to the activation of zinc-like transcription factor Gli, while the latter gets into the nucleus causing the transcription of the target genes. Therefore, in the Hh signaling pathway, Hh is the starting point of the signaling pathway, and Gli as the transcription factor is the end of the signaling pathway, with Hh and SMO as the activator, PTCH as a suppressor, regulating the signaling pathway activity[12,14].

The transmembrane protein receptor SMO, a key member of the Hh signaling pathway, is the information converter in the Hh signaling pathway. It can convert extracellular Hh signals into intracellular Gli1 signal, which initiates gene transcription within the nucleus and activates the Hh signaling pathway[15]. The majority of the occurrence and development process of tumor cells related to Hh pathway activation has SMO functional mutation. Small molecule SMO protein antagonists specifically block the Hh signaling pathway by blocking SMO, whereas the Hh signaling pathway is inactivated in normal adults, so the antagonist does not have side effects on other parts of the body, which is theoretical basis of the feasibility of targeting treatment of the tumor. Therefore, SMO protein has become one of the most interesting targets in the development of anti-tumor drugs. The synthesis of small molecule antagonists targeting SMO protein has also become a hotspot in the international pharmaceutical companies. Today there are at least five small molecule antagonists targeting SMO protein in clinical trials. Among them, small molecule SMO antagonist GDC-0449 co-developed by United States Genentech and Curis, was approved for the treatment of advanced basal cell cancer patients by the US Food and Drug Administration (FDA) in January 2012[16]. This proves that small molecule SMO antagonists have good application value and market prospect as anti-tumor drug research and development.

The hedgehog (Hh) signaling pathway has been implicated in regulations of patterning, growth and cell migration during embryonic development. In adult cells, Hh signaling pathway is limited to tissue maintenance and repair. However, this pathway is reactivated during tissue repair and regeneration Under normal conditions, the endogenous ligands sonic hedgehog, Indian hedgehog and desert hedgehog bind to their receptor Patched (PTCH) which in turn relieves the inhibitory effect of PTCH on smoothened (Smo), a downstream protein. Smo activation triggers a series of events ultimately lead to specific gene expression mediated by the Gli family transcription factors (Jiang and Hui, *Dev. Cell Review* (2008) 15:801-812). Aberrant Hh signaling has been linked to numerous human cancers. Mutational inactivation of the inhibitory pathway components leads to constitutive ligand-independent activation of the Hh signaling pathway, results in cancers such as basal cell carcinoma and medulloblastoma (Xie et al., *Nature* (1998) 391:90-92), glioblastoma (Bar et al. *Stem Cells* (2007) 25(10):2524-33; Filbin et al. *Nature Medicine* (2013) 19:1518-1523dio:10.10.38/nm.3328). Ligand-dependent activation of Hh signaling is involved in prostate cancer (Sanchez et al. *PNAS* 101(2004) (34):12561-566), pancreatic cancer (Thayer et al. *Nature* (2003) 423:851-856), breast cancer (Kubo et al. *Cancer Res.* (2003) 64:6071-6074), non-small cell lung cancer (Yuan et al. *Oncogene* (2007) 26:1046-1055), small cell lung cancer (Watkins et al. *Nature* (2003) 422:313-317), and some blood cancers (Scales et al., *Trends Pharmacol. Sci.* (2009) 30:303-312). Therefore, inhibition of the aberrant Hh signaling represents a promising approach toward novel anticancer therapy (Peukert and Miller-Moslin, *ChemMedChem* (2010) 5:500-512).

It has been found that hedgehog signaling regulates the expression of the ABC transporter proteins multi-drug resistance protein-1 (MDR1, ABCB1, P-glycoprotein) and (BCRP, ABCG2), and that targeted knockdown of MDR1 and BCRP expression by small interfering RNA partially reverses Hh-induced chemoresistance. This indicates the Hh pathway maybe a target to overcome MDR and increase chemotherapeutic response (Sims-Mourtada et al. *Oncogene* (2007) 26:5674-79). The blockade of sonic hedgehog signaling pathway was found to enhance the antiproliferative effect of EGFR inhibitors in pancreatic cancer cells (Hu et al. *Acta Pharmacol. Sin.* (2007) 28 1224-30) and prostate cancer cells (Mimeault et al. *Int. J. Cancer* (2006) 118:1022-31).

The hedgehog pathway has also been associated with tumor regrowth after chemoradiotherapy and as a potential target to improve radiation response (Sim-Mourtada et al. *Clin. Cancer Res.* (2006) 12:6565-6572).

It has also been reported that the inhibition of the hedgehog signaling pathway may be of use for the treatment of a range of diseases related to inflammation, epithelial cell hyperplasia, fibrosis of tissue or immune disorders (Lamb et al. EP1183040).

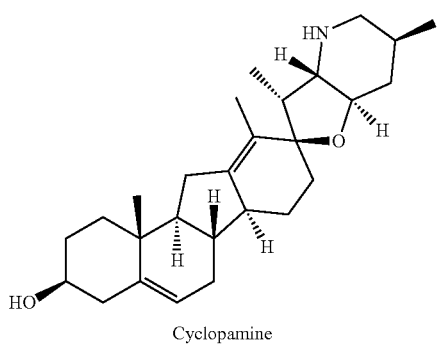

Cyclopamine

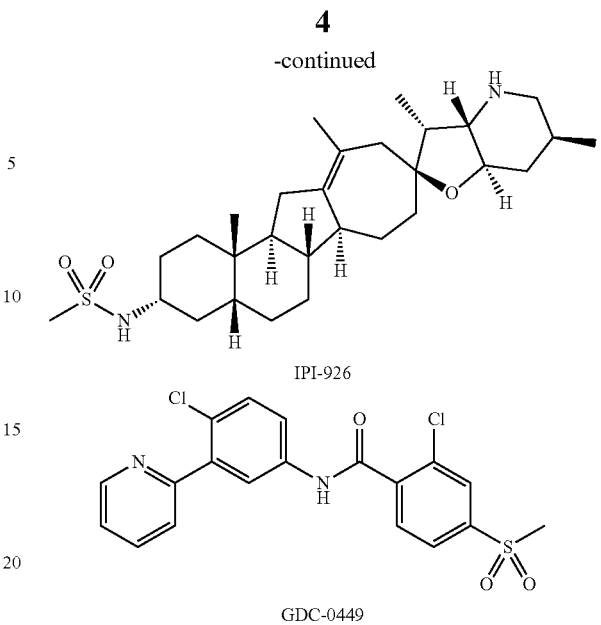

IPI-926

GDC-0449

Cyclopamine, a naturally occurring alkaloid, was the first reported Hh signaling pathway inhibitor (Cooper et al., *Science* (1998) 280:1603-1607), and later identified as Smo antagonist (Chen et al., *Genes. Dev.* (2002) 16:2743-2748). A cyclopamine derivative IPI-926, which demonstrated better potency, stability and other pharmaceutical properties than that of cyclopamine, has entered clinical development (Trembley et al., *J Med. Chem.* (2009) 52:4400-4418). One embryonic pathway inhibitor, GDC-0449 (Robarge et al., *Bioorg. Med. Chem. Lett.* (2009) 19: 5576-5581), was approved by FDA in January 2012 for the treatment of basal cell carcinoma which is not suitable for operation.

Despite advances with these compounds, there are numerous problems. For example, GDC-0449 possesses all sp2-hybridized carbons but one, thereby resulting in high melting point (251° C.) and poor solubility (9.5 μg/mL)—the enhanced solubility was obtained by adding an ortho-chloro group to the right side ring to introduce tilt and reduce planarity of the aryl amide (Robarge et al.). It also introduced mutations in SMO and resulted rapid tumor relapse in at least one patient (Yauch et al., *Science* (2009) 326:572-574).

We have disclosed a series of compounds in a previous patent (WO2014113191A1), wherein the representative compounds (A-55 and A97) have a structure represented below, whose inhibitory activities (IC$_{50}$ of NIH3T3-GRE-Luc) against Hh signaling pathway were 5.5 nM (reference vismodegib 8.8 nM, ratio 1.6-fold) and 84 nM (reference vismodegib 45 nM, ratio 0.54-fold), respectively.

Formula I

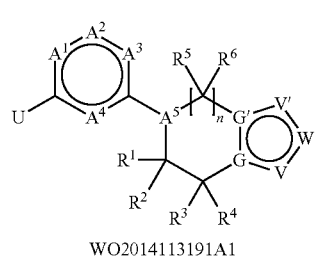

WO2014113191A1

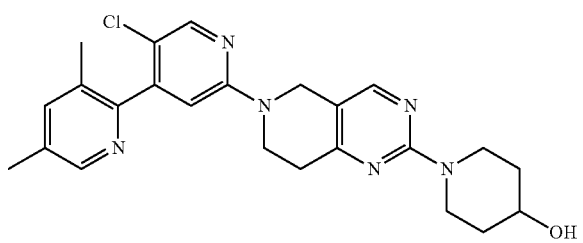

IC$_{50}$: 5.5 nM
(vismodegib 8.8 nM)

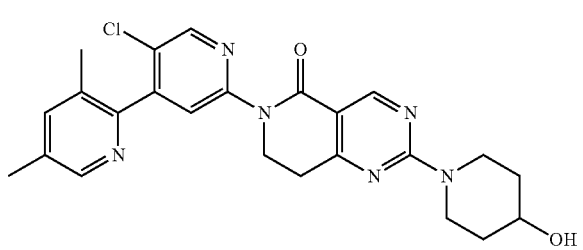

IC$_{50}$: 84 nM
(vismodegib 45 nM)

When the R$^5$ and R$^6$ of the series of compounds (Formula I) in WO2014113191A1 were hydrogen, the activity was better. However, subsequent pharmacokinetic studies have found that the methylene moieties of the compounds (Formula I in WO2014113191A1, R$^5$ and R$^6$ were hydrogen) were susceptible to oxidative metabolism.

OTHER PUBLICATIONS

1. Jemal, A.; Siegel, R.; Weingerg. R. A. Cancer statistics, 2010. *CA. Cancer J Cli.,* 2010, 144, 277-300.
2. Workman, P.; Collins, I. Modern Cancer Drug Discovery: Integrating Targets, Technologies and Treatments. In *Cancer Drug Design and Discovery,* 1 st ed.; Neidle, S., Ed.; Elsevier: New York, 2008; pp 3-38.
3. di Magliano, M. P.; Hebrok, M. Hedgehog signalling in cancer formation and maintenance. *Nat. Rev. Cancer* 2003, 3, 903-911.
4. Beachy, P. A.; Karhadkar, S. S.; Berman, D. M. Tissue repair and stem cell renewal in carcinogenesis. *Nature* 2004, 432, 324-331.
5. Dahmane, N.; Lee, J.; Robins, P.; Heller, P.; Ruizi Altaba, A. Activation of the transcription factor Gli1 and the sonic Hedgehog signaling pathway in skin tumours. *Nature* 1997, 389, 876-881.
6. Hutchin, M. E.; Kariapper, M. S. T.; Gratchtchouk, M.; Wang, A.; Wei, L.; Cummings, D.; Liu, J.; Michael, L. R.; Glick, A.; Dlugosz, A. A. Sustained Hedgehog signaling is required for basal cell carcinoma proliferation and survival: Conditional skin tumorigenesis recapitulates the hair growth cycle. *Genes Dev.* 2004, 19, 214-224.
7. Kubo, M.; Nakamura, M.; Tasaki, A.; Yamanaka, N.; Nakashima, H.; Nomura, M.; Kuroki, S.; Katano, M. Hedgehog signaling pathway is a new therapeutic target for patients with breast cancer. *Cancer Res.* 2004, 64, 6071-6074.
8. Berman, D. M.; Karhadkar, S. S.; Maitra, A.; Montes de Oca, R.; Gerstenblith, M. R.; Briggs, K.; Parker, A. R.; Shimada, Y.; Eshleman, J. R.; Watkins, D. N.; Beachy, P. A. Widespread requirement for Hedgehog ligand stimulation in growth of digestive tract tumors. *Nature* 2003, 425, 846-851.
9. Goodrich, L. V.; Scott, M. P. Hedgehog and Patched in neural development and disease. *Neuron* 1998, 21, 1243-1257.
10. Stecca, B.; Mas., C.; Clement, V.; Zbinden, M.; Correa, R.; Piguet, V.; Beermann, F.; Ruiz, A. Melanomas require Hedgehog-Gli signaling regulated by interactions between Gli1 and the RAS-MEK/AKT pathways. *Proc. Natl. Acad. Sci. U.S.A.* 2007, 104, 5895-5900.
11. Thayer, S. P.; PascadiMagliano, M.; Heiser, P. W.; Nielsen, C. M.; Roberts, D. J.; Lauwers, G. Y.; Qi, Y. P.; Gysin, S.; Fernandez-delCastillo, C.; Yajnik, V.; Antoniu, B.; McMahon, M.; Warshaw, A. L.; Hebrok, M. Hedgehog is an early and late mediator of pancreatic cancer tumorigenesis. *Nature* 2003, 425, 851-856.
12. Lum, L.; Beachy, P. A. The Hedgehog response network: sensors, witches, and routers. *Science* 2004, 304, 1755-1759.
13. Beachy, P. A.; Karhadkar, S. S.; Berman, D. M. Tissue repair and stem cell renewal in carcinogenesis. *Nature* 2004, 432, 324-331.
14. PascadiMagliano, M.; Hebrok, M. Hedgehog signalling in cancer formation and maintenance. *Nat. Rev. Cancer* 2003, 3, 903-911.
15. Romer, J. T.; Kimura, H.; Magdaleno, S.; Sasai, K.; Fuller, C.; Baines, H.; Connelly, M.; Stewart, C. F.; Gould, S.; Rubin, L. L.; Curran, T. Suppression of the Shh pathway using a small molecule inhibitor eliminates medulloblastoma in Ptc1(+/−)p53(−/−) mice. *Cancer Cell* 2004, 6, 229-240.
16. Curis Pharmaceuticals press release: http://investors-.curis.com/releasedetail.cfm?ReleaseID=643756.

SUMMARY

In view of the prior art mentioned above, it is an objective of the present disclosure to provide a chiral heterocyclic compound with Hedgehog pathway antagonist activity and its preparation method and use thereof. Said compound can block the Hedgehog pathway, thereby inhibiting abnormal cell growth and block metastasis and regeneration of tumor cells.

The objective of the present disclosure can be achieved by the following technical scheme:

A chiral heterocyclic compound with Hedgehog pathway antagonist activity, and pharmaceutically acceptable salts thereof, having a structure represented by formula I:

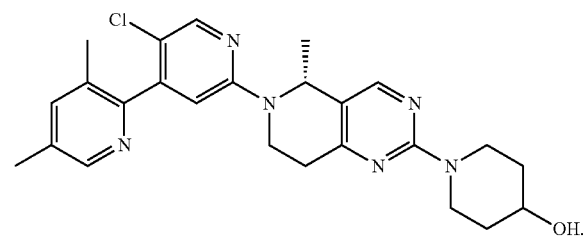

A method for preparing the chiral heterocyclic compound with Hedgehog pathway antagonist activity is also provided in the present disclosure, comprising: oxidizing the methylthio of compound

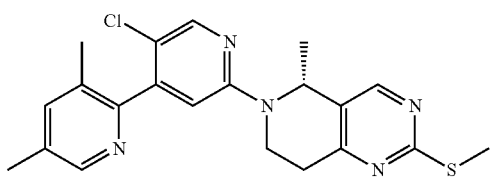

and reacting thus-obtained methylsulfonyl intermediate with 4-hydroxypiperazine to obtain the compound I.

In the preparation method mentioned above, said

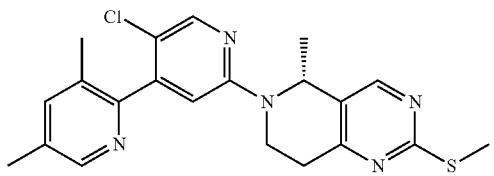

can be prepared by a coupling reaction between compound

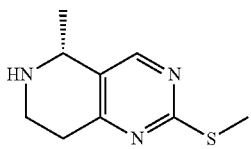

and compound

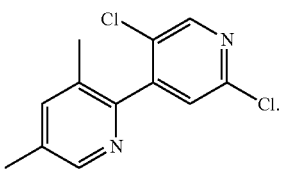 [SMILES: Cc1cnc(-c2cc(Cl)ncc2Cl)c(C)c1]

In the preparation method mentioned above, said

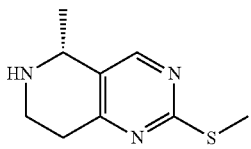

can be prepared by the following steps: mixing (1S, 2S)-(+)-N-p-toluenesulfonyl-1,2-diphenylethylenediamine, dichloro (p-methyl cumene) ruthenium (II) dimer, amine and formic acid-acetonitrile solution to give a mixed solution; mixing compound

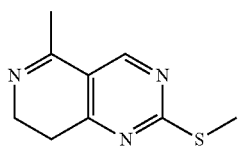

in acetonitrile solution with said mixed solution obtained above to react; adjusting the pH of the system to 8 by adding sodium bicarbonate; performing extraction and purification.

In the preparation method mentioned above, concentration of formic acid in its acetonitrile solution can be about 2-3.5 mmol/mL; concentration of compound

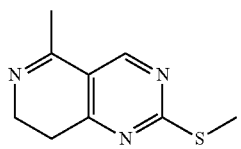

in its acetonitrile solution can be about 0.1~1 mmol/mL.

Use of the chiral heterocyclic compound with Hedgehog pathway antagonist activity for the preparation of anti-tumor drugs or anti-tumor pharmaceutical compositions is also provided in the present disclosure. Said tumor includes liver cancer, lung cancer, rectal cancer, cervical cancer, pancreatic cancer, breast cancer, gastric cancer, oral cancer, esophageal cancer, nasopharyngeal carcinoma, skin cancer, bone cancer, brain cancer, kidney cancer and blood cancer or a combination of several.

An anti-tumor pharmaceutical composition is also provided in the present disclosure, comprising a composition of said chiral heterocyclic compound with Hedgehog pathway antagonist activity and a combination of at least two pharmaceutically acceptable salts thereof.

The present disclosure also provides a combined application composition for anti-tumor drugs, comprising a combination of one or more of cisplatin, paclitaxel, camptothecin, trastuzumab, Gleevec®, imatinib, gefitinib, erlotinib and lapatinib in combination with the chiral heterocyclic compound with Hedgehog pathway antagonist activity as described above.

The present disclosure also provides a combined application composition for antitumor drugs, comprising a combination of one or more of cisplatin, paclitaxel, camptothecin, trastuzumab, Gleevec®, imatinib, gefitinib, erlotinib and lapatinib in combination with the anti-tumor pharmaceutical composition as described above.

The chiral heterocyclic compound with Hedgehog pathway antagonist activity provided in the present disclosure is a new type of anti-tumor compound which has a chiral carbon in its structure with R configuration. The inhibitory activity of the chiral compound on Hedgehog pathway can be increased by about 3-fold compared to the racemic compound. In the inhibition experiment of CYP liver enzyme in vitro, the inhibitory activity of the racemic compound to CYP-2C9 was 52% at 10 µM, whereas the chiral compound has an inhibitory activity against CYP-2C9 of only 26% at 10 µM, showing a better safety performance. In the rat pharmacokinetic test, the bioavailability of the chiral compound can be nearly doubled to 100% compared to the racemic compound. In addition, the area under the curve and other parameters can also be significantly improved. In the mouse tumor model, the racemic compound can only stop the tumor growth at a dose of 100 mg/kg, while the chiral compound can shrink the tumor volume to almost undetectable, thus demonstrating a stronger antitumor effect. Compared with A-55 in the previous patent (WO2014113191A1), which was a demethyl analog, the inhibitory activity of the chiral compound against Hedgehog pathway can increase about 12 folds. In the pharmacokinetic test of rats, the bioavailability of the chiral compound can be nearly doubled to 100% compared to compound A-55; in vivo half-life can increase as well; drug exposure (area under the curve AUC) can significantly increase. This suggests that the chiral compound, compared to its corresponding demethyl analog, can have more prominent and unexpected effects on inhibiting abnormal cell growth and blocking metastasis and regeneration of tumor cells, displaying many advantages such as better activity, better bioavailability, and the like, thereby having a better application prospect of tumor treatment.

The beneficial effect of the present disclosure is: chiral heterocyclic compound with Hedgehog pathway antagonist activity can block the Hedgehog pathway, thereby inhibiting abnormal cell growth, blocking metastasis and regeneration of tumor cells. The chiral heterocyclic compound of the present disclosure can also have better biological activities and better pharmacokinetic properties compared to its demethyl analog, with a better application prospect of tumor treatment.

Embodiments of the present disclosure will now be described in further detail with reference to the accompanying drawings, based on which the present disclosure is more readily understood.

In one aspect, the present invention provides compounds of Formula II:

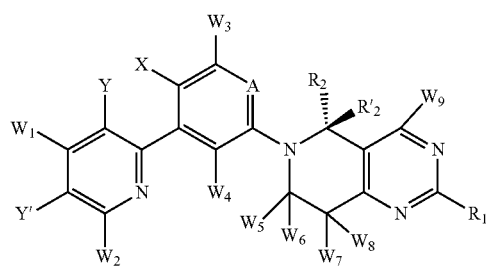

Formula II or a pharmaceutically acceptable salt, stereoisomer, or solvate thereof, wherein X, Y and Y' are independently $C_{1-3}$ alkyl, $CD_3$, $CF_3$, CN, halide, or OMe;

$R_2$ and $R'_2$ are independently H, $C_{1-3}$ alkyl, $CD_3$, or $CF_3$, with the proviso that at least one of $R_2$ and $R'_2$ is not H;

$R_1$ is —NRxRy, wherein Rx and Ry are independently H, alkyl, cycloalkyl, alkylcycloalkyl, C(O)R", or —NRxRy together to form a 4-7 membered heterocycle, wherein the 4-7 membered heterocycle is substituted or unsubstituted;

R" is $C_{1-5}$ alkyl;

$W_1$, $W_2$, $W_3$, $W_4$, $W_5$, $W_6$, $W_7$, $W_8$ and $W_9$ are independently H or D; and A is N or CH.

In some embodiments, Y and Y' are independently $CH_3$, $CD_3$, $CF_3$, Cl or F. In some embodiments, X is halide, $CF_3$, $CD_3$ or $CH_3$. In some embodiments, $R_1$ is

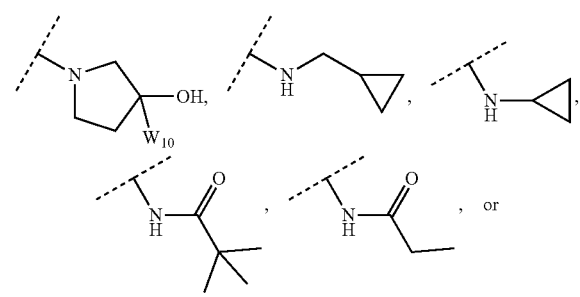

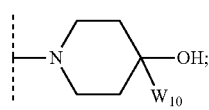

and $W_{10}$ is H or D. In some embodiments, $R'_2$ is H or D; and $R_2$ is $C_{1-3}$ alkyl or $CF_3$. In some embodiments, $R'_2$ is H or D; and $R_2$ is $CH_3$ or $CD_3$. In some embodiments, A is N. In some embodiments, the compound is selected from the group consisting of:

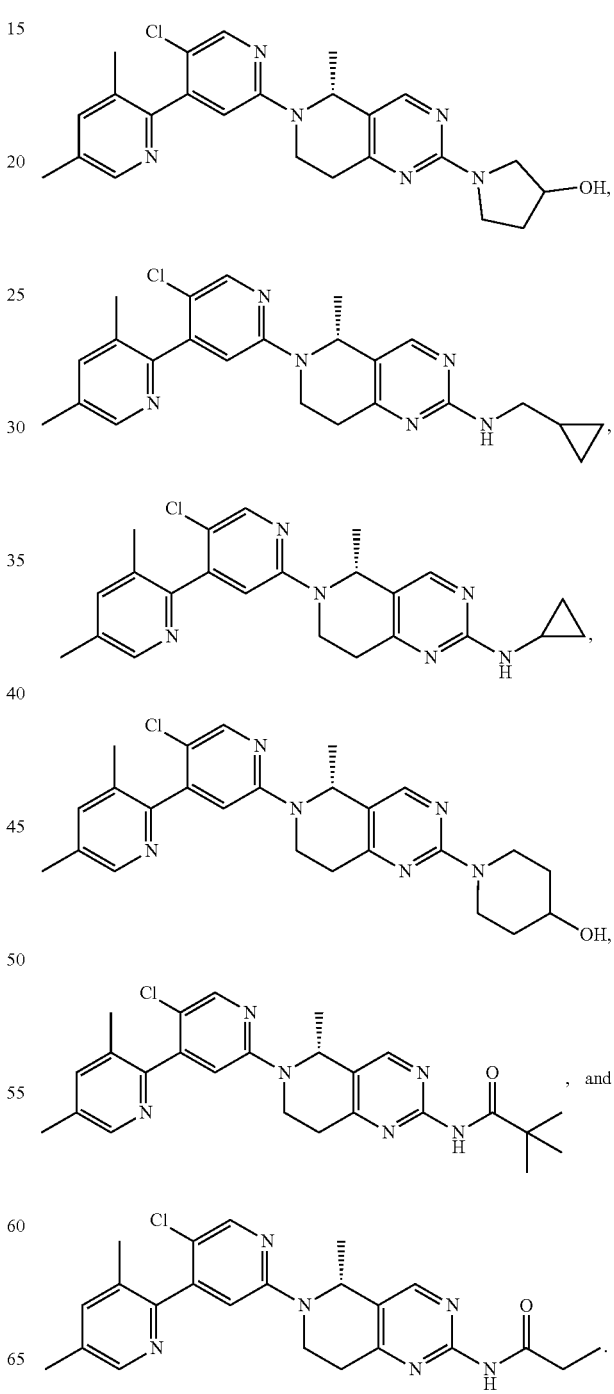

In another aspect, herein provides compounds of Formula III:

Formula III or a pharmaceutically acceptable salt, stereoisomer, or solvate thereof, wherein $R_2$ and $R'_2$ are independently H, $C_{1-3}$ alkyl, $CD_3$, or $CF_3$, with the proviso that at least one of $R_2$ and $R'_2$ is not H;

$R_1$ is —NRxRy, wherein Rx and Ry are independently H, alkyl, cycloalkyl, alkylcycloalkyl, C(O)R", or —NRxRy together to form a 4-7 membered heterocycle, wherein the 4-7 membered heterocycle is substituted or unsubstituted;

R" is $C_{1-5}$ alkyl;

$W_1$, $W_2$, $W_3$, $W_4$, $W_5$, $W_6$, $W_7$, $W_8$ and $W_9$ are independently H or D; and A is N or CH.

In some embodiments, $R_1$ is and $W_{10}$ is H or D. In some embodiments, $R'_2$ is H or D; and $R_2$ is $C_{1-3}$ alkyl or $CF_3$. In some embodiments, $R'_2$ is H or D; and $R_2$ is $CH_3$ or $CD_3$. In some embodiments, A is N.

In still another aspect, herein provides compounds of Formula IV:

Formula IV or a pharmaceutically acceptable salt, or solvate thereof, wherein $R_2$ is $C_{1-3}$ alkyl, $CD_3$, or $CF_3$;

$R_1$ is —NRxRy, wherein Rx and Ry are independently H, alkyl, cycloalkyl, alkylcycloalkyl, C(O)R", or —NRxRy together to form a 4-7 membered heterocycle, wherein the 4-7 membered heterocycle is substituted or unsubstituted;

R" is $C_{1-5}$ alkyl; and $W_1$, $W_2$, $W_3$, $W_4$, $W_5$, $W_6$, $W_7$, $W_8$ and $W_9$ are independently H or D.

In some embodiments, $R_1$ is and $W_{10}$ is H or D. In some embodiments, $R_2$ is $C_{1-3}$ alkyl or $CF_3$. In some embodiments, $R_2$ is $CH_3$ or $CD_3$.

In one aspect, herein provides pharmaceutical composition comprising a compound of any of Formulas II-IV, and a pharmaceutically acceptable carrier.

In still another aspect, herein provides a method for inhibiting an activation of a hedgehog-patched pathway in a patient diagnosed with a hyperproliferative disorder, comprising administering to the patient a composition comprising a hedgehog pathway inhibitor in an effective amount to reduce the activation of the hedgehog-patched pathway in a cell of the patient, wherein the hedgehog pathway inhibitor is a compound of any of Formulas II-IV.

Figure 1:
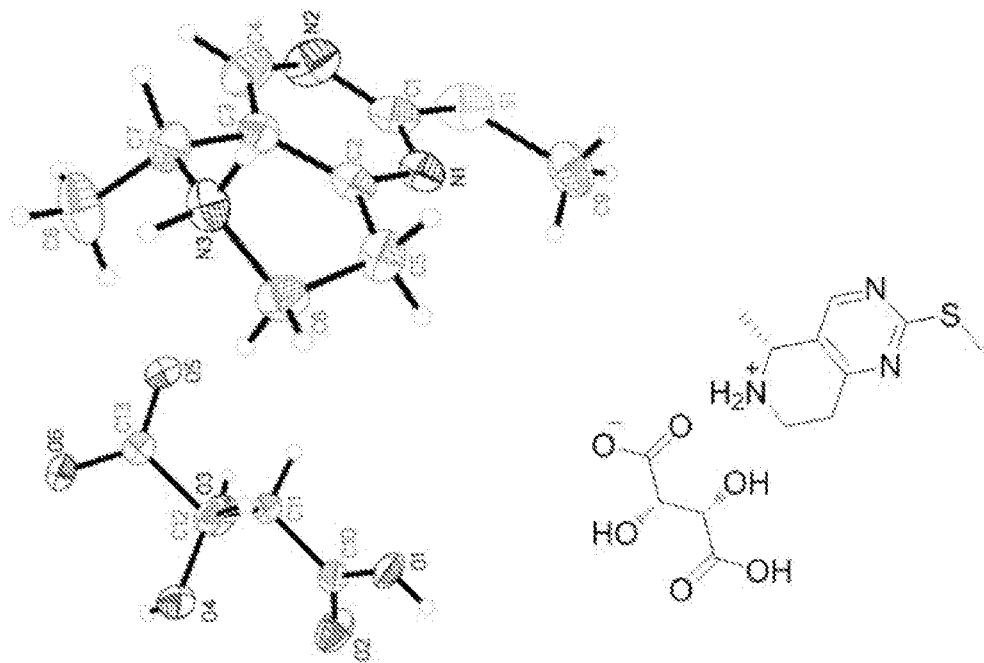
FIG. 1 is a single crystal diffraction pattern of the D-tartrate salt of intermediate B1-3 in Example 1.

Before proceeding with the detailed description, it is to be appreciated that the following detailed description is merely exemplary in nature and is not intended to limit the invention or the application and uses thereof. Hence, although the present disclosure is, for convenience of explanation, depicted and described as shown in certain illustrative embodiments, it will be appreciated that it can be implemented in various other types of embodiments and equivalents, and in various other systems and environments. Furthermore, there is no intention to be bound by any theory presented in the preceding background or the following detailed description.

DETAILED DESCRIPTION OF THE INVENTION

Definitions

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms.

As used herein, the term "alkyl" refers to a straight or branched chain saturated aliphatic hydrocarbon. Alkyl groups include groups having from 1 to 8 carbon atoms ($C_{1-8}$ alkyl), from 1 to 6 carbon atoms ($C_{1-6}$ alkyl) and from 1 to 4 carbon atoms ($C_{1-4}$ alkyl), including, for example, methyl, ethyl, propyl, isopropyl, n-butyl, sec-butyl, tert-butyl, pentyl, 2-pentyl, isopentyl, neopentyl, hexyl, 2-hexyl, 3-hexyl and 3-methylpentyl. In some instances, a substituent of an alkyl group is specifically indicated. For example, "cyanoalkyl" refers to an alkyl group substituted with at least one cyano substituent.

"Alkenyl" refers to straight or branched chain alkene groups, which comprise at least one unsaturated carbon-carbon double bond. Alkenyl groups include $C_{2-8}$ alkenyl, $C_{2-6}$ alkenyl and $C_{2-4}$ alkenyl groups, which have from 2 to 8, 2 to 6 or 2 to 4 carbon atoms, respectively, including, for example, ethenyl, allyl or isopropenyl. "Alkynyl" refers to straight or branched chain alkyne groups, which have one or more unsaturated carbon-carbon bonds, at least one of which is a triple bond. Alkynyl groups include $C_{2-8}$ alkynyl, $C_{2-6}$ alkynyl and $C_{2-4}$ alkynyl groups, which have from 2 to 8, 2 to 6 or 2 to 4 carbon atoms, respectively.

A "cycloalkyl" is a group that comprises one or more saturated rings in which all ring members are carbon, including, for example, cyclopropyl, cyclobutyl, cyclopentyl, cyclohexyl, cycloheptyl, cyclooctyl, adamantyl. Cycloalkyl groups do not comprise an aromatic ring or a heterocyclic ring. Certain cycloalkyl groups are $C_{3-7}$ cycloalkyl, in which the cycloalkyl group contains a single ring having from 3 to 7 ring members, all of which are carbon. A "cycloalkenyl" is a group that comprises one or more unsaturated rings in which all ring members are carbon.

"Alkoxy" is meant an alkyl group as described above attached via an oxygen bridge. Alkoxy groups include $C_{1-6}$ alkoxy and $C_{1-4}$ groups, which have from 1 to 6 or from 1 to 4 carbon atoms, respectively. Methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy are representative alkoxy groups.

"Alkylamino" refers to a secondary or tertiary amine that has the general structure —NH-alkyl or —N(alkyl)(alkyl), wherein each alkyl is selected independently from alkyl, cycloalkyl and (cycloalkyl)alkyl groups. Such groups include, for example, mono- and di-($C_{1-6}$ alkyl)amino groups, in which each $C_{1-6}$ alkyl may be the same or different. It will be apparent that the definition of "alkyl" as used in the term "alkylamino" differs from the definition of "alkyl" used for all other alkyl-containing groups, in the inclusion of cycloalkyl and (cycloalkyl)alkyl groups.

"Halogen" means fluorine, chlorine, bromine, and iodine. A "haloalkyl" is an alkyl group that is substituted with 1 or more independently chosen halogens (e.g., "$C_{1-6}$ haloalkyl" groups have from 1 to 6 carbon atoms and at least one halogen). Examples of haloalkyl groups include, but are not limited to, mono-, di- or tri-fluoromethyl; mono-, di- or tri-chloromethyl; mono-, di-, tri-, tetra- or penta-fluoroethyl; mono-, di-, tri-, tetra- or penta-chloroethyl; and 1,2,2,2-tetrafluoro-1-trifluoromethyl-ethyl.

A "heteroaryl" is an aromatic group in which at least one aromatic ring comprises at least one heteroatom selected from N, O and S. Heteroaryls include, for example, 5-12 membered heteroaryls. Examples included but are not limited to imidazole, furan, furazan, isothiazole, isoxazole, oxadiazole, oxazole, pyrazine, pyrazole, pyridazine, pyridine, pyrimidine, tetrazole, thiazole and thiophene.

The term "heterocyclic" or "heterocycle" refers to a ring structure containing 3-12 ring atoms, in which at least one ring atom is carbon and at least one ring atom is a heteroatom selected from N, O, and S. A heterocyclic group may be aromatic or non-aromatic. Piperidine and oxetane are non-limiting examples of non-aromatic heterocycles. Thiazole and pyridine are non-limiting examples of aromatic heterocycles.

A "substituent" and "substituted," as used herein, denote that a molecular moiety is covalently bonded to an atom within a molecule of interest. For example, a ring substituent may be a moiety such as a halogen, alkyl group, haloalkyl group or other group that is covalently bonded to an atom (preferably a carbon or nitrogen atom) that is a ring member. Substituents of aromatic groups are generally covalently bonded to a ring carbon atom. Similarly a chain substituent may be a moiety such as a halogen, alkyl group, haloalkyl group or other group that is covalently bonded to an atom (preferably a carbon or nitrogen atom) that is a member of the chain.

The term "pharmaceutically acceptable" when used with reference to a compound of Formulas II-IV is intended to refer to a form of the compound that is safe for administration to a subject. For example, a free base, a salt form, a solvate, a hydrate, a prodrug or derivative form of a compound of Formulas II-IV, which has been approved for mammalian use, via oral ingestion or any other route of administration, by a governing authority or regulatory agency, such as the Food and Drug Administration (FDA) of the United States, is pharmaceutically acceptable.

Included in the compounds of Formulas II-IV are the pharmaceutically acceptable salt forms of the free-base compounds. The term "pharmaceutically-acceptable salts" embraces salts, commonly used to form alkali metal salts and to form addition salts of free acids or free bases, which have been approved by a regulatory agency. Salts are formed from ionic associations, charge-charge interactions, covalent bonding, complexation, coordination, etc. The nature of the salt is not critical, provided that it is pharmaceutically acceptable.

In some embodiments, the compound(s) of Formulas II-IV is used to treat a subject by administering the compound(s) as a pharmaceutical composition. To this end, the compound(s), in one embodiment, is combined with one or more pharmaceutically acceptable excipients, including carriers, diluents or adjuvants, to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective amount" is intended to quantify the amount of each agent, which will achieve the goal of improvement in disorder severity and the frequency of incidence over treatment of each agent by itself, while avoiding adverse side effects typically associated with alternative therapies. The effective amount, in one embodiment, is administered in a single dosage form or in multiple dosage forms.

Regardless of the route of administration selected, the compounds of the present invention, which may be used in a suitable hydrated form, and/or the pharmaceutical compositions of the present invention, are formulated into pharmaceutically acceptable dosage forms or by other conventional methods known to those of skill in the art.

Actual dosage levels of the active ingredients in the pharmaceutical compositions of the present invention may be varied so as to obtain an effective amount of the active ingredient to achieve the desired therapeutic response for a particular patient, composition, and mode of administration, without being toxic to the patient.

The selected dosage level will depend upon a variety of factors including the activity of the particular compound of the present invention employed, the route of administration, the time of administration, the rate of excretion of the particular compound being employed, the duration of the treatment, other drugs, compounds and/or materials used in combination with the particular hedgehog inhibitor employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day. The mode of administration can have a large effect on dosage. Higher doses may be used for localized routes of delivery.

If desired, the effective daily dose of the active compound may be administered as two, three, four, five, six or more sub-doses administered separately at appropriate intervals throughout the day, optionally, in unit dosage forms. Those of skill in the art will readily appreciate that dose levels can vary as a function of the specific compound, the severity of the symptoms and the susceptibility of the subject to side effects. Dosages for a given compound disclosed herein are readily determinable by those of skill in the art by a variety of means.

NOVEL COMPOUNDS

Compounds A-55 and A-97 shown below were disclosed among a series of compounds in WO2014113191A1. Compounds A-55 and A-97 were reported to display $IC_{50}$ values in the primary assay, vide supra, of 5.5 nM (in term of relative efficacy, about 1.6 folds of vismodegib (8.8 nM)), and 84 nM (in term of relative efficacy, about 0.5 fold of vismodegib (45 nM)), respectively. However, the desmethyl compound A-55 exhibited is easy to metabolized via benzylic oxidation at the C-5 methylene group of the tetrahydropyrido[4,3-d]pyrimidine ring. The benzylic oxidative metabolism may lead to formation of dihydroisoquinolinium-like metabolite, a reactive metabolite may cause toxicities (DMD 34:1310-1316, 2006). Accordingly, blocking this benzylic oxidation site in the tetrahydropyrido[4,3-d]pyrimidine ring is desirable.

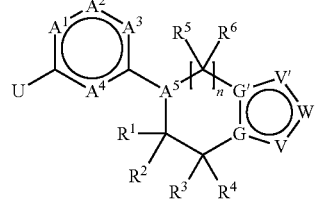

Formula I

WO2014113191A1

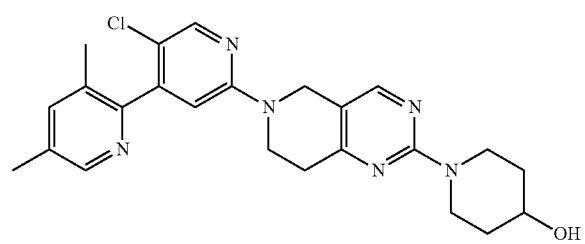 [SMILES: Cc1cnc(-c2cc(N3CCc4nc(N5CCC(O)CC5)ncc4[C@H]3C)ncc2Cl)c(C)c1]

A-55

$IC_{50}$: 5.5 nM
(vismodegib 8.8 nM)

A-97

IC₅₀: 84 nM
(vismodegib 45 nM)

In some cases, the present disclosure prepared hedgehog pathway inhibitors shown in Formulas II:

Formula II or a pharmaceutically acceptable salt, stereoisomer, or solvate thereof, wherein X, Y and Y' are independently $C_{1-3}$ alkyl, $CD_3$, $CF_3$, CN, halide, or OMe;

$R_2$ and $R'_2$ are independently H, $C_{1-3}$ alkyl, $CD_3$, or $CF_3$, with the proviso that at least one of $R_2$ and $R'_2$ is not H;

$R_1$ is —NRxRy, wherein Rx and Ry are independently H, alkyl, cycloalkyl, alkylcycloalkyl, C(O)R", or —NRxRy together to form a 4-7 membered heterocycle, wherein the 4-7 membered heterocycle is substituted or unsubstituted;

R" is $C_{1-5}$ alkyl;

$W_1$, $W_2$, $W_3$, $W_4$, $W_5$, $W_6$, $W_7$, $W_8$ and $W_9$ are independently H or D; and A is N or CH.

In some cases, the present disclosure prepared hedgehog pathway inhibitors shown in Formulas II:

Formula II or a pharmaceutically acceptable salt, stereoisomer, or solvate thereof, wherein X, Y and Y' are independently $C_{1-3}$ alkyl, $CD_3$, $CF_3$, CN, halide, or OMe;

$R_2$ and $R'_2$ are independently H, $C_{1-3}$ alkyl, $CD_3$, or $CF_3$, with the proviso that at least one of $R_2$ and $R'_2$ is not H;

$R_1$ is —NRxRy, wherein Rx and Ry are independently H, alkyl, cycloalkyl, alkylcycloalkyl, C(O)R", or —NRxRy together to form a 4-7 membered heterocycle, wherein the 4-7 membered heterocycle is substituted or unsubstituted;

R" is $C_{1-5}$ alkyl;

$W_1$, $W_2$, $W_3$, $W_4$, $W_5$, $W_6$, $W_7$, $W_8$ and $W_9$ are independently H or D; and A is N or CH.

In some cases, the present disclosure prepared chiral hedgehog pathway inhibitors shown in Formulas IV:

Formula IV or a pharmaceutically acceptable salt, or solvate thereof, wherein $R_2$ is $C_{1-3}$ alkyl, $CD_3$, or $CF_3$;

$R_1$ is —NRxRy, wherein Rx and Ry are independently H, alkyl, cycloalkyl, alkylcycloalkyl, C(O)R", or —NRxRy together to form a 4-7 membered heterocycle, wherein the 4-7 membered heterocycle is substituted or unsubstituted;

R" is $C_{1-5}$ alkyl; and $W_1$, $W_2$, $W_3$, $W_4$, $W_5$, $W_6$, $W_7$, $W_8$ and $W_9$ are independently H or D.

In some cases, the present disclosure provided methods of making compounds of Formula II-IV. For example, Scheme 1 below depicts steps that can be used to make compounds of Formula IV. In some cases, the thiomethyl group in Intermediate A can be oxidized to produce a methylsulfonyl intermediate, which can be displaced by NHRxRy to produce a compound of Formula IV.

Scheme 1

Intermediate A

Formula III

In some cases, Intermediate A can be produced from a coupling reaction between intermediates B and C, as shown in Scheme 2 below.

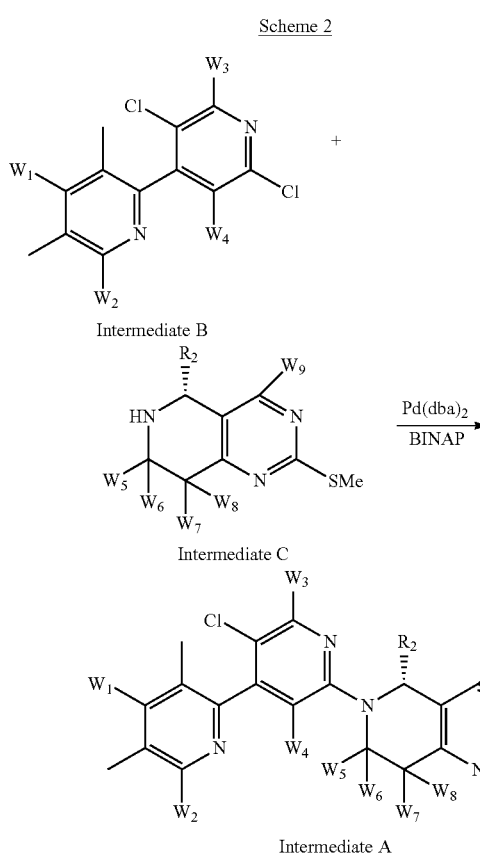

Scheme 2

Intermediate B

Intermediate C

Intermediate A

In some cases, Intermediate C can be prepared from a reduction reaction of Intermediate D as shown in Scheme 3 below.

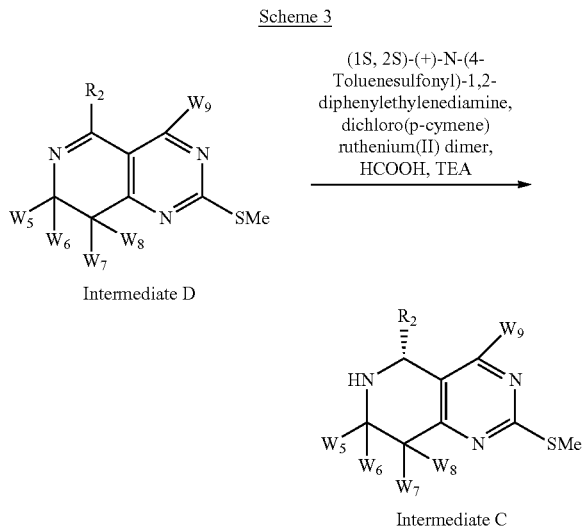

Scheme 3

Intermediate D

Intermediate C

In some cases, the reduction in Scheme 3 can be conducted when the formic acid is kept at from about 2 mmol/mL to about 3.5 mmol/mL. In some cases, the reduction in Scheme 3 can be conducted when Intermediate D is kept at from about 0.1 mmol/mL to about 1.0 mmol/mL.

In some cases, the present disclosure discloses a chiral compound of Formula IV, which comprises an R-configuration chiral carbon at C-5 position of the tetrahydropyrido [4,3-d]pyrimidine ring. For example compound B1 in Table 5, vide infra, can be about three times more potent than its racemic counterpart, compound B. In some cases, in in vitro cytochrome P450 (CYP) inhibition assay showed that racemic compound B (at 10 μM) can display about 52% inhibition of CYP-2C9 while the chiral compound B1 (at 10 μM) can display about 26% inhibition % inhibition of CYP-2C9. Comparing with the racemic compound B, the chiral compound B1 is likely to have less Drug-Drug-Interaction (DDI) potential with the drugs metabolized by CYP-2C9.

In some cases, pharmacokinetics experiments can show that the bioavailability of chiral compound B1 can be doubled when compared with racemic compound B to reach close to about 100%. In addition, area under the curve (AUC) measurements can be improved as well for the chiral compound B1 over racemic compound B.

In some cases, in a mouse tumor model, at 100 mg/kg dosage, racemic compound B can stop the tumor from growing. In contrast, in mouse tumor model, chiral compound B can reduce the size of the tumor over time, and, in selected cases, can reduce the size of the tumor drastically to reach the level of close to unrecognizable sizes.

In some cases, when compared with compound A-55, the desmethyl analog of compound B1, the chiral compound B1 can almost double the bioavailability of the drug, increase the half-life of the drug inside the animal body, improve AUC.

PHARMACEUTICAL COMPOSITIONS/FORMULATIONS

One embodiment provides a pharmaceutical composition comprising a compound of Formulas II-IV, or a stereoisomer, tautomer, hydrate, solvate or pharmaceutically acceptable salt thereof, and at least one pharmaceutically acceptable excipient.

In some embodiments, the present invention provides methods for regulating the hedgehog pathway. The method comprises administrating to a mammalian subject a therapeutically effective amount of at least one compound of Formulas II-IV. The method comprises treating or preventing basal cell carcinoma, breast carcinoma, cervical carcinoma, colorectal cancer, gliomas carcinoma, hepatocellular carcinoma, leukemia, lung carcinoma, lymphoma, medulloblastoma, multiple myeloma, oral carcinoma, ovary cancer, pancreas carcinoma, prostate cancer, stomach carcinoma, upper GI cancer, esophageal carcinoma, nasopharyngeal carcinoma, dermal carcinoma, osteocarcinoma, kidney cancer, and sarcoma.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: *The Science and Practice of Pharmacy*, Nineteenth Ed., Easton, Pa.: Mack Publishing Company (1995); Hoover, John E., *Remington's Pharmaceutical Sciences*, Mack Publishing Co., Easton, Pa. (1975); Liberman, H. A. and Lachman, L., Eds., *Pharmaceutical Dosage Forms*, Marcel Decker, New York, N.Y. (1980); and *Pharmaceutical Dosage Forms and Drug Delivery Systems*, Seventh Ed., Lippincott Williams & Wilkins (1999), herein incorporated by reference for such disclosure.

A pharmaceutical composition, as used herein, refers to a mixture of a compound of Formula II with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

All formulations for oral administration are in dosages suitable for such administration. Examples of such dosage units are tablets or capsules. In some embodiments, these contain an amount of active ingredient from about 1 to 2000 mg, advantageously from about 1 to 500 mg, and typically from about 5 to 150 mg. A suitable daily dose for a human or other mammal vary widely depending on the condition of the patient and other factors, but, once again, can be determined using routine methods and practices.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethylcellulose (HPMC), hydroxypropyl-methylcellulose phthalate, hydroxypropylmethylcellulose acetate stearate (HPMCAS), sucrose, xylitol, lactitol, mannitol, sorbitol, sodium chloride, polyethylene glycol, and the like.

Suitable disintegrants for use in the solid dosage forms described herein include, but are not limited to, natural starch such as corn starch or potato starch, a pregelatinized starch, or sodium starch glycolate, a cellulose such as methylcrystalline cellulose, methylcellulose, microcrystalline cellulose, croscarmellose, or a cross-linked cellulose, such as cross-linked sodium carboxymethylcellulose, cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a gum such as agar, guar, locust bean, Karaya, pectin, or tragacanth, sodium starch glycolate, bentonite, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethyl-cellulose, methylcellulose, hydroxypropylmethylcellulose, hydroxypropylmethylcellulose acetate stearate, hydroxyethylcellulose, hydroxypropylcellulose, ethylcellulose, and microcrystalline cellulose, microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose, glucose, dextrose, molasses, mannitol, sorbitol, xylitol, lactose, a natural or synthetic gum such as acacia, tragacanth, ghatti gum, mucilage of isapol husks, starch, polyvinylpyrrolidone, larch arabogalactan, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Binder levels of up to 70% in tablet formulations are common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinyl-pyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Methods of the present invention include the use of at least one compound of Formulas II-IV, which inhibits hedgehog signaling in the regulation of repair and/or functional performance of a wide range of cells, tissues and organs, and have therapeutic and cosmetic applications ranging from regulation of neural tissues, bone and cartilage formation and repair, regulation of spermatogenesis, regulation of smooth muscle, regulation of lung, liver and other organs arising from the primitive gut, regulation of hematopoietic function, regulation of skin and hair growth, etc. Accordingly, the methods and compositions of the present invention include the use of the subject inhibitors for all such uses as inhibitors of hedgehog proteins may be implicated. Moreover, the subject methods can be performed on cells which are provided in culture (in vitro), or on cells in a whole animal (in vivo).

The examples and preparations provided below illustrated and exemplify the compounds described herein and methods of preparing such compounds. In general, the compounds described herein may be prepared by processes known in the general chemical arts.

The compounds of the present invention can be prepared using various synthetic routes, including those described below, starting from commercially available materials. Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Functional groups may be removed according to known procedures in the art.

MATERIALS AND METHODS

All reagents and solvents were obtained commercially. When required, all reagents and solvents were purified by standard techniques: tetrahydrofuran was purified by distillation from sodium. All thin-layer chromatography (TLC) analyses were performed on silica gel (Qingdao Haiyang Chemical Co. Ltd.) and spots revealed by UV visualization at 254 nm and $I_2$ vapor or phosphomolybdic acid. All nuclear magnetic resonance spectra were recorded using a Varian unity INOVA 400NB spectrometer at 400 MHz or a Varian Vnmrs spectrometer at 300 MHz as indicated. LC-MS was run using an Agilent 1100 system using an Agela Durashell C18 3.5 μm 4.6×50 mm column. Gradients were run using 0.1 trifluoroacetic acid/water and acetonitrile with gradient 5/95 to 95/5 in the run time indicated.

The technical solution of the present disclosure can now be described in detail in order to provide a clearer understanding of the technical features, objects and advantages of the present disclosure, but are not to be construed as limiting the scope of the invention. The experimental methods described in the examples below are conventional methods, if without special instructions; the reagents and materials are commercially available, unless otherwise specified. The solvents and drugs used were either analytically pure or chemically pure; the solvent was re-distilled prior to use; the anhydrous solvent was treated in accordance with standard or documented methods. Column chromatography silica gel (100~200 mesh) and thin layer chromatography silica gel (GF254) were products of Qingdao marine chemical factory and Yantai chemical factory. If not specified, the eluent was petroleum ether (60° C.~90° C.)/ethyl acetate (v/v); the chromogenic reagent was iodine or phosphomolybdic acid-ethanol solution; all the extraction solvent was dried using anhydrous $Na_2SO_4$. $^1$H-NMR was recorded on a Bruck-400 nuclear magnetic resonance instrument and TMS was used as internal standard. LC-MS was recorded using a high-performance liquid chromatography-ion trap mass spectrometer (LC-MSD Trap), a diode array detector (DAD), detection wavelengths of 214 nm and 254 nm, ion trap mass spectrometry (ESI). HPLC column was Agela Durashell C18 (4.6×50 mm, 3.5 μm); the mobile phase was 0.1% $NH_4HCO_3$ aqueous solution: acetonitrile (5:95 to 95:5 in 5 min); the flow rate was 1.8 mL/min.

Example 1

The present example provided a chiral heterocyclic compound with Hedgehog pathway antagonist activity (B1), which has an R configuration. The compound was prepared by the following method:

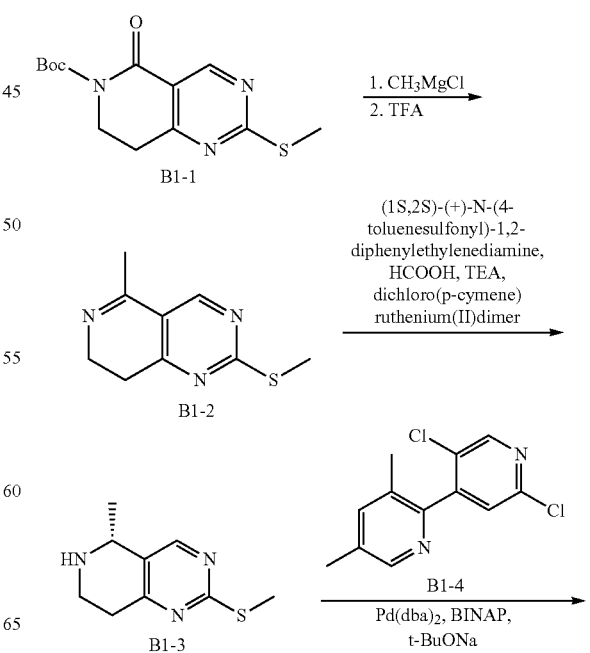

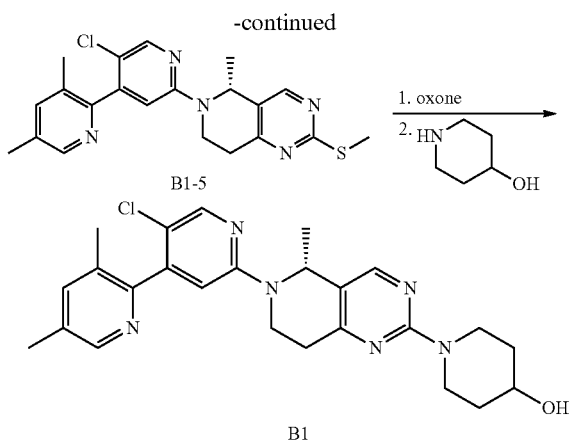

1) Synthesis of Intermediate B1-2:

B1-1 (4.3 g, 14.576 mmol) was dissolved in 40 mL of tetrahydrofuran and methylmagnesium chloride solution (3.0 M in THF, 5.3 mL, 15.9 mmol) was added at −60° C. After 2 hours of reaction, the reaction mixture was quenched with water (30 mL), extracted with ethyl acetate (30 mL×3), and the organic phase was dried and concentrated by anhydrous sodium sulfate. The residue was dissolved in 20 mL of dichloromethane and 10 mL of trifluoroacetic acid, and the reaction was stirred at room temperature for 5 hours. The solvent was taken out by spin and 10 mL of water was added. The pH of the system was adjusted to 8-9 with saturated sodium bicarbonate. The aqueous phase was extracted with dichloromethane (20 ml×3) and dried; after concentration, it was purified by column chromatography (petroleum ether: ethyl acetate=4:1) to yield a yellow solid B1-2 (1.7 g, 60%). The NMR data of B1-2 was as below:

$^1$HNMR (400 MHz, CDCl$_3$) δ 8.50 (s, 1H), 3.85 (t, J=6.8 Hz, 2H), 2.82 (t, J=7.2 Hz, 2H), 2.60 (s, 3H), 2.37 (s, 3H).

2) Synthesis of Intermediate B1-3:

(1S, 2S)-(+)-N-p-toluenesulfonyl-1,2-diphenylethylenediamine (209 mg, 0.57 mmol) and dichloro (p-methyl cumene) ruthenium (II) (174 mg, 0.28 mmol) were added to a 250 mL flask; triethylamine (2.3 g, 22.8 mmol) and formic acid (2.6 g, 56.5 mmol) in acetonitrile (20 mL) were added under nitrogen protection. After stirring for 10 minutes, a solution of intermediate B1-2 (2.2 g, 11.4 mmol) in acetonitrile (40 mL) was added and the reaction was stirred at room temperature overnight. The reaction was quenched with 10 mL of water and the pH was adjusted to 8 with saturated sodium bicarbonate. After extraction of acetonitrile, dichloromethane (40 ml×5) was added and the organic phases were combined and dried. The crude product (1.4 g) was obtained by spin drying and column chromatography purification (dichloromethane:methanol=100:1 to 50:1). The crude product was dissolved in 20 mL methanol and a solution of D(−)-tartaric acid (1.4 g, 9.3 mmol) in methanol (15 mL) was added, refluxed at 70° C. for 10 hours, filtered at room temperature. The solid was recrystallized using methanol to yield D-tartrate of intermediate B1-3 (1.1 g). The results of single crystal diffraction test were shown in FIG. 1, demonstrating that it has a R configuration.

The resulting D-tartrate of intermediate B1-3 was dissolved in water (10 mL) and the pH was adjusted to 8. The aqueous phase was extracted with dichloromethane (30 ml×5), dried and concentrated to yield B1-3 (483 mg, 21%). $^1$HNMR (400 MHz, CDCl$_3$) δ 8.29 (s, 1H), 4.14 (q, J=6.7 Hz, 1H), 3.42~3.35 (m, 1H), 3.15~3.09 (m, 1H), 3.01~2.93 (m, 1H), 2.87~2.80 (m, 1H), 2.55 (s, 3H), 1.51 (d, J=6.4 Hz, 3H).

3) Synthesis of Intermediate B1-5:

The intermediate B1-3 (130 mg, 0.67 mmol), B1-4 (168 mg, 0.67 mmol) and sodium tert-butoxide (128 mg, 1.33 mmol) were dissolved in 10 mL of toluene, and Pd(dba)$_2$ (38 mg, 0.067 mmol) and BINAP (42 mg, 0.067 mmol) were added under nitrogen protection. The reaction was stirred at 120° C. overnight. After cooling, the reaction solution was filtered. Filtrate underwent spin drying and column chromatography purification (petroleum ether: ethyl acetate=5:1) to yield a yellow oil as B1-5 (50 mg, 18%).

4) Synthesis of Product B1:

The intermediate B1-5 (35 mg, 0.085 mmol) and 2 mL of tert-butanol were added to 50 mL sealed tube and then the potassium persulfate complex salt (65 mg, 0.21 mmol) was added and reacted for 5 hours. 4-hydroxypiperidine (86 mg, 0.85 mmol) was dissolved in 5 mL tert-butyl alcohol and added to the reaction and heated to 90° C. overnight. After cooling, the solvent was removed by spin drying, and common salt solution (20 mL) was added. Extraction was performed with ethyl acetate (10 ml×3). The organic phases were combined, dried, concentrated and purified by column chromatography (petroleum ether:ethyl acetate=2:1) to yield a white solid (11 mg, 24%) B1. Its structure was represented as below:

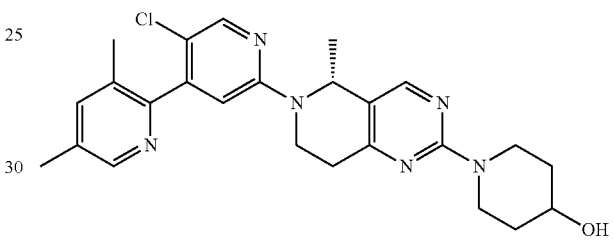

The NMR data of B1 was as below: $^1$HNMR (400 MHz, CDCl$_3$) δ 8.35 (s, 1H), 8.21 (s, 1H), 8.10 (s, 1H), 7.43 (s, 1H), 6.60 (s, 1H), 5.35 (s, 1H), 4.47~4.31 (m, 3H), 3.98~3.88 (m, 1H), 3.45~3.36 (m, 1H), 3.30~3.24 (m, 2H), 2.93~2.85 (m, 1H), 2.78~2.72 (m, 1H), 2.38 (s, 3H), 2.18 (s, 3H), 2.00~1.90 (m, 2H), 1.54~1.50 (m, 2H), 1.42 (d, J=6.8 Hz, 3H); ee=97%; [α]$^{25.9}_D$=−50.0 (c=0.5, CHCl$_3$).

Example 2

The present example provided a chiral heterocyclic compound with Hedgehog pathway antagonist activity (B2), which has an S configuration. The compound was prepared by the following method:

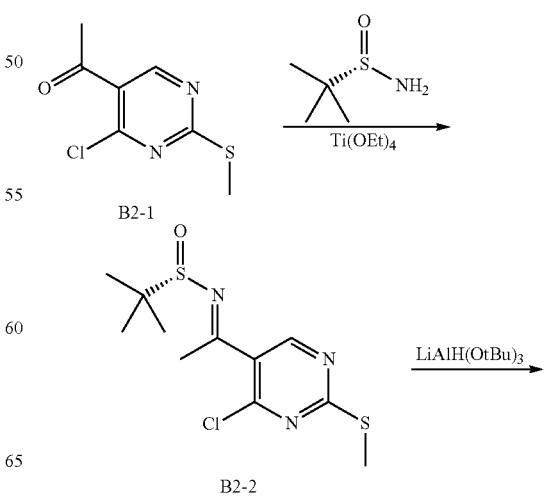

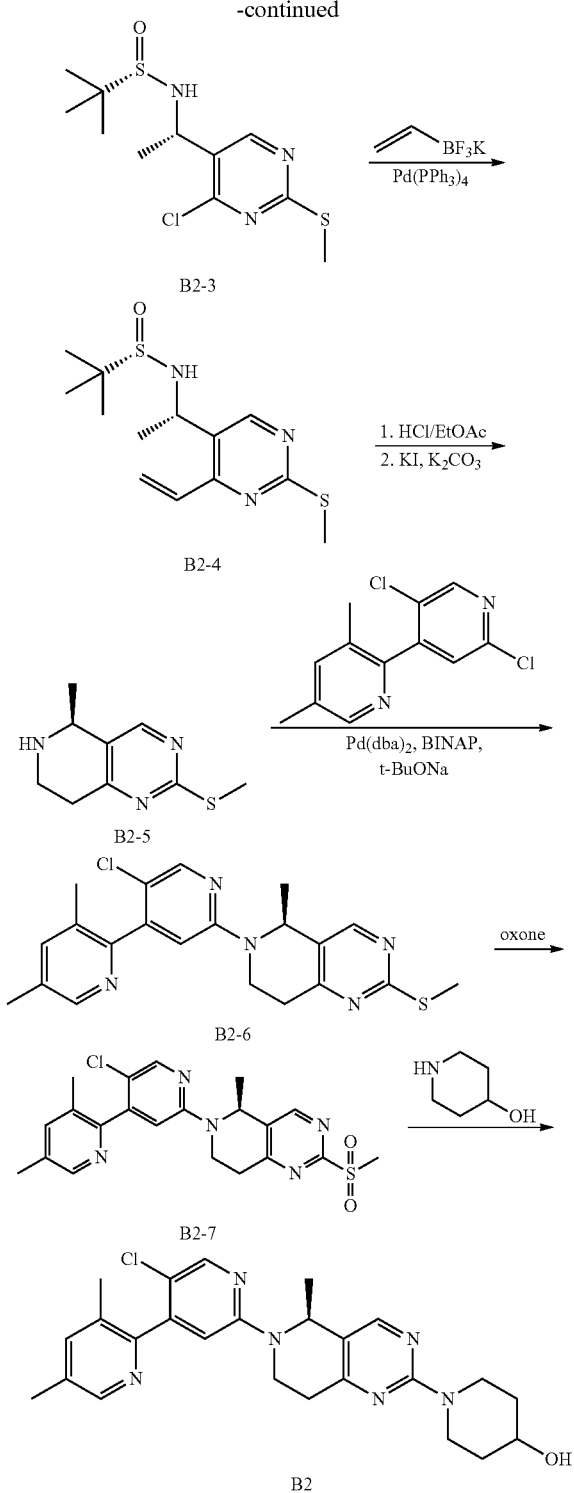

step. The NMR data of intermediate B2-2 was as below: $^1$H NMR (400 MHz, CDCl$_3$) δ 8.51 (s, 1H), 2.76 (s, 3H), 2.60 (s, 3H), 1.31 (s, 9H).

2) Synthesis of Intermediate B2-3:

The intermediate B2-2 (500 mg, 1.6 mmol) was dissolved in anhydrous tetrahydrofuran (25 mL) and lithium tri-t-butoxyaluminum hydride (1.245 g, 4.9 mmol) was slowly added at 0° C. Reaction was continued at this temperature for 40 minutes. The reaction mixture was quenched with water, diluted with ethyl acetate (50 mL) and filtered. The filtrate was dried using sodium sulfate and spin drying was performed. The residue was purified by column chromatography (petroleum ether:ethyl acetate=5:1) to yield a yellow oil B2-3 220 mg, 43%). The NMR data of B2-3 was as below: $^1$HNMR (400 MHz, CDCl$_3$) δ 8.54 (s, 1H), 4.85~4.78 (m, 1H), 3.77 (s, 1H), 2.56 (s, 3H), 1.58 (d, J=6.4 Hz, 3H), 1.24 (s, 9H).

3) Synthesis of Intermediate B2-4:

The intermediate B2-3 (21 mg, 0.018 mmol), potassium terephthalate (72 mg, 0.54 mmol), tetrakylphenylphosphine palladium (21 mg, 0.018 mmol) and cesium fluoride (108 mg, 0.71 mmol) were added to a mixed solvent of Dioxane (10 mL) and water (2 mL), the reaction solution was heated to 105° C. under nitrogen protection and reacted for 2 hours. The reaction solution was cooled to room temperature, filtered, and the filtrate was diluted with ethyl acetate (40 mL). The organic phase was washed with saturated common salt solution and dried. After the solvent was removed by spin, the residue was purified by column elution (petroleum ether:ethyl acetate=5:1) to yield a yellow oil as B2-4 (100 mg, 93%) of which the NMR data was as below: $^1$H NMR (400 MHz, CDCl$_3$) δ 8.56 (s, 1H), 7.08~7.01 (m, 1H), 6.74~6.70 (m, 1H), 5.74~5.71 (m, 1H), 4.84~4.77 (m, 1H), 3.41 (s, 1H), 2.59 (s, 3H), 1.57 (d, J=6.4 Hz, 3H), 1.23 (s, 9H).

4) Synthesis of Intermediate B2-5:

Intermediate B2-4 (330 mg, 1.1 mmol) was dissolved in 4 mL of ethyl acetate and a 2M solution of hydrogen chloride in ethyl acetate (2 mL) was added. After the reaction solution was stirred at room temperature for 5 hours, the solvent was removed by spin; the residue was dissolved in water (10 mL) and potassium carbonate (305 mg, 2.2 mmol) and potassium iodide (183 mg, 1.1 mmol) were added. The reaction was carried out at 100° C. with stirring for 16 hours. The reaction solution was extracted with dichloromethane (20 mL×4) and the combined organic phases were dried and followed by spin drying to yield a yellow oil as B2-5 (88 mg, 40%) of which the NMR data was as below: $^1$HNMR (400 MHz, CDCl$_3$) δ 8.30 (s, 1H), 4.20~4.13 (m, 1H), 3.44~3.37 (m, 1H), 3.18~3.10 (m, 1H), 3.04~2.96 (m, 1H), 2.91~2.82 (m, 1H), 2.55 (s, 3H), 1.53 (d, J=6.4 Hz, 3H).

5) Synthesis of Intermediate B2-6:

The intermediate B2-5 (88 mg, 0.45 mmol), B1-4 (137 mg, 0.54 mmol) and sodium tert-butoxide (86 mg, 0.90 mmol) were dissolved in 10 mL of toluene; Pd (dba)$_2$ (26 mg, 0.045 mmol) and BINAP (28 mg, 0.045 mmol) were added under nitrogen protection; and the reaction was stirred at 120° C. overnight. After cooling, the reaction solution was filtered. Filtrate underwent spin drying and column chromatography purification (petroleum ether:ethyl acetate=5:1) to yield a yellow oil as B2-6 (40 mg, 21%) of which the NMR data was as below: $^1$H NMR (400 MHz, CDCl$_3$) δ 8.36 (s, 1H), 8.32 (s, 1H), 8.22 (s, 1H), 7.43 (s, 1H), 6.64 (s, 1H), 5.54 (s, 1H), 4.41~4.33 (m, 1H), 3.46~3.39 (m, 1H), 1) Synthesis of Intermediate B2-2:

B2-1 (1.8 g, 8.9 mmol), tetraethyl titanate (6 g, 26 mmol) and S-tert-butylsulfenamide (2.14 g, 17.7 mmol) were dissolved in anhydrous dioxane (40 mL) and heated to 90° C. for 2 hours. The reaction solution was cooled to room temperature and the solvent was removed. The residue was diluted with ethyl acetate (150 mL) and quenched with a small amount of water. The solid was removed by filtration and the filtrate was dried and underwent spin drying to yield the intermediate B2-2 which was used directly for the next 3.07~2.98 (m, 1H), 2.94~2.86 (m, 1H), 2.56 (s, 3H), 2.38 (s, 3H), 2.18 (s, 3H), 1.48 (d, J=6.8 Hz, 3H). 6) Synthesis of product B2:

The intermediate B2-6 (40 mg, 0.1 mmol) and 10 mL of tert-butanol were added to 50 mL sealed tube and then the potassium persulfate complex salt (76 mg, 0.25 mmol) was added and reacted for 5 hours. 4-hydroxypiperidine (40 mg, 0.4 mmol) was added and heated to 90° C. for reaction overnight. After cooling, the solvent was removed by spin drying, and common salt solution (20 mL) was added. Extraction was performed with ethyl acetate (20 ml×3). The organic phases were combined, dried, concentrated and purified by column chromatography (petroleum ether:ethyl acetate=2:1 to 1:1) to yield a white solid (11 mg, 24%) B2, of which the NMR data was as below: $^1$HNMR (400 MHz, CDCl$_3$) δ8.35 (s, 1H), 8.21 (s, 1H), 8.10 (s, 1H), 7.42 (s, 1H), 6.61 (s, 1H), 5.35 (s, 1H), 4.48-4.38 (m, 2H), 4.35-4.27 (m, 1H), 3.99-3.87 (m, 1H), 3.50-3.36 (m, 1H), 3.32-3.21 (m, 2H), 2.96-2.84 (m, 1H), 2.79-2.70 (m, 1H), 2.37 (s, 3H), 2.18 (s, 3H), 1.99-1.90 (m, 2H), 1.54-1.48 (m, 2H), 1.43 (d, J=6.8 Hz, 3H);

ee=97%; $[\alpha]^{26.7}_D$=+54.0 (c=0.2, CHCl$_3$).

Example 3

In this example, the compounds B1 and B2 obtained in Example 1 and 2 and the corresponding racemic compound B were subjected to NIH3T3-GRE-Luc luciferase reporter assay to verify that the obtained compounds have effect on blocking Hedgehog pathway.

NIH3T3 cells (CRL-1658, ATCC) were maintained in DMEM (Gibico) supplemented with 10% FBS (Hyclone). GRE-Luc plasmid was generated by inserting 8×Gli-1 responsive element (GRE) into the multiple cloning site of pGL4.26 vector (Promega). NIH3T3-GRE-Luc reporter cell line was established by hygromycin (Invitrogen) selection after transfected with GRE-Luc luciferase reporter plasmid. Single clones were validated by the induction of luciferase by recombinant sonic hedgehog (sHh) protein or small molecule agonist SAG (ABIN629346). Selected clone was used to monitor the Hh signaling.

The NIH3T3-GRE-Luc cells were maintained in complete culture medium (DMEM with 4 mM L-Gln, 1.5 g/L sodium bicarbonate and 4.5 g/L glucose supplemented with 100 μg/mL hygromycin and 10% FBS). When confluent, the cells were trypsinized and re-suspended in assay medium (0.5% serum-containing DMEM). After 100 L/well of cells suspension was added to the 96-well-plate (Final cell concentration is 15,000 cells/well), cells were cultured for additional 48 hours before adding the compounds.

Compounds were serially diluted in DMSO and further diluted with assay medium. In an embodiment, 10 nM SAG was added in assay medium as the agonist of Hh signaling. After the compounds and agonist were prepared, the medium was removed carefully. 100 μL of assay medium containing compound and agonist was added to the cell with care. Cell plates were incubated at 37° C. for additional 48 hours.

Following the 48 hours incubation, 40 μL/well of luciferase media (Brigh-Glo, Promega) was added to the cells. The plate was incubated at room temperature for 5 minutes under gentle shaking. Luminescence signal was measured with plate reader (PHERAstar FS, BMG). The potency of compounds was calculated based on the inhibition of luminescence signaling.

Figure 2:
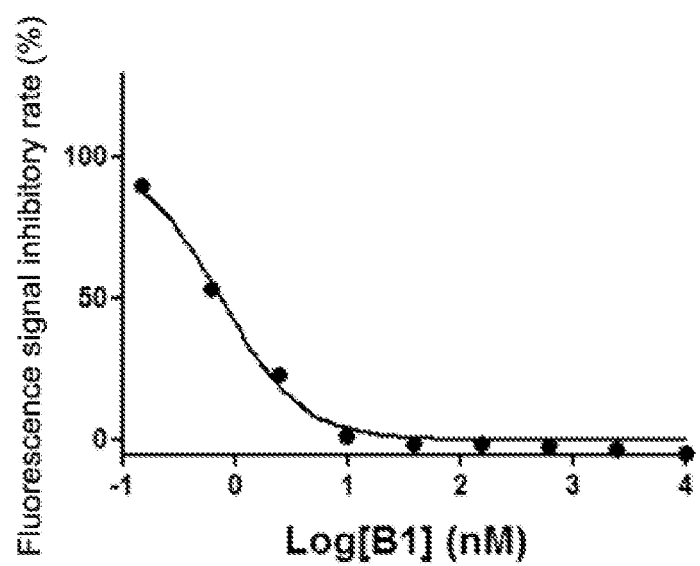
FIG. 2 is a graph showing the inhibitory activity of compound B1 in Example 3 against Hh pathway.
Figure 3:
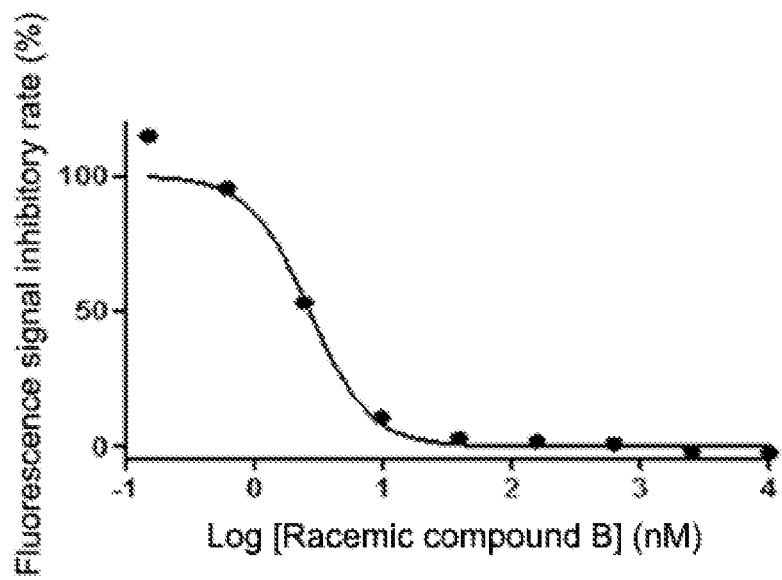
FIG. 3 is a graph showing the inhibitory activity of compound B in Example 3 against Hh pathway.
Figure 4:
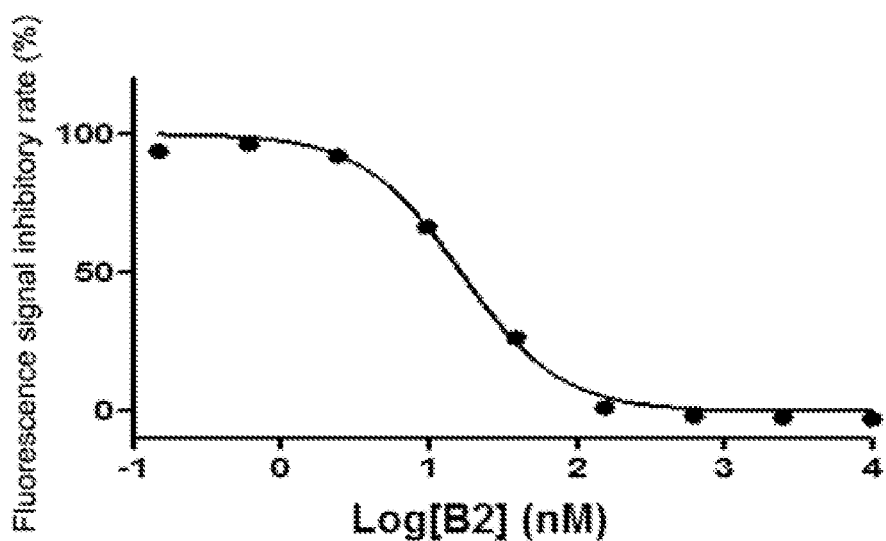
FIG. 4 is a graph showing the inhibitory activity of compound B2 in Example 3 against Hh pathway.

In this example, the bioactivity of compounds B1 and B2 in the examples and the racemic compound B was measured according to NIH3T3-GRE-Luc luciferase reporter assay described above. The small molecule SMO antagonist GDC-0449 was used as a control drug. The results were shown in Table 1 and FIG. 2-4.

TABLE 1

| Test compounds | Structural formula | Effect IC$_{50}$ (nM)(GRE reporter assay) | Effect IC$_{50}$ (nM)(GRE reporter assay: vismodegib) | Ratio |
| --- | --- | --- | --- | --- |
| B1 | [structure] | 0.8 | 17.9 | 22.4 |
| B2 | [structure] | 17 | 19.3 | 1.1 |

TABLE 1-continued

| Test compounds | Structural formula | Effect IC$_{50}$ (nM)(GRE reporter assay) | Effect IC$_{50}$ (nM)(GRE reporter assay: vismodegib) | Ratio |
|---|---|---|---|---|
| Racemic compound B | 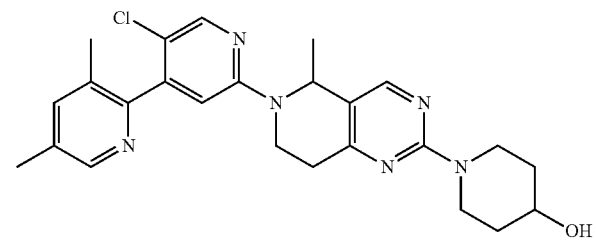 [SMILES: Cc1cnc(-c2cc(N3CCc4nc(N5CCC(O)CC5)ncc4C3C)ncc2Cl)c(C)c1] | 2.7 | 13.4 | 5.0 |

The results show that compound B2 of S configuration has a relatively poor Hh pathway inhibitory activity and is not important for the treatment of diseases associated with Hh signaling pathway. Compound B1 of R configuration was the optimal compound, which has a 3-fold increase on Hh pathway inhibitory activity compared to racemic compound B, more than 20-fold of the compound B2 of S configuration. Compared to the racemic compound B and the compound B2 of S configuration, compound B1 of R configuration can better inhibit the Hh signaling pathway, thus providing a better therapeutic application prospect for diseases associated with the Hh signaling pathway and avoiding the potential side effects associated with the presence of the S configuration compound B2.

Example 4

In this example, the CYP liver enzyme inhibition experiment was carried out for the R configuration compound B1 obtained in Example 1 and the racemic compound B to evaluate the in vitro safety of R configuration compound B1 and racemic compound B.

Experiment Procedure:

The five major CYP isozymes and their respective probe substrates were: CYP-1A2 (phenacetin, 30 μM), CYP-2C9 (toluenesulfonylurea, 100 μM), CYP-2C19 40 μM), CYP-2D6 (dextromethorphan, 5 μM) and CYP-3A4 (midazolam, 1 μM). All probes were used close to or below their KMS concentrations. The mixture (200 μL) was incubated in a 37° C. constant temperature water bath, containing HLM (0.2 mg/mL), phosphate buffer (100 mM, pH 7.4), NADPH (1 μM), test compound (10 μM) and the respective CYP probe substrate. Before the reaction with NADPH, the mixture was pre-incubated for 10 minutes to undergo inhibitor-enzyme interaction. After a specific period of time (10 minutes for CYP-1A2, 2D6 and 3A4; 30 minutes for CYP-2C9 and 2C19), the reaction was quenched by addition to 100 μL solution of appropriate amount of cold acetonitrile. Reaction system was centrifuged and injected into the LC-MS/MS to quantify the concentration of specific metabolite formed from the substrate and the CYP enzyme. Each test compound was tested at least three times independently. The results were shown in Table 2.

TABLE 2

| Compound | CYP-3A4 Inhibitory rate (%) | CYP-2D6 Inhibitory rate (%) | CYP-1A2 Inhibitory rate (%) | CYP-2C9 Inhibitory rate (%) | CYP-2C19 Inhibitory rate (%) |
|---|---|---|---|---|---|
| H$_2$O | 0.0 ± 9.7 | 0.0 ± 9.3 | 0.0 ± 7.4 | 0.0 ± 4.3 | 0.0 ± 4.4 |
| Positive control | 96 ± 0.23 | 94 ± 1.0 | 95 ± 0.8 | 81 ± 1.4 | 58 ± 1.2 |
| Racemic compound B | 21 ± 4.0 | 30 ± 1.7 | 21 ± 1.3 | 52 ± 5.2 | 44 ± 3.3 |
| B1 | 20 ± 5.9 | 24 ± 3.5 | 22 ± 15 | 26 ± 6.0 | 43 ± 2.6 |

The results showed that the inhibitory rates of R configuration compound B1 and racemic compound B were similar among four of the five main CYP isozymes. However, the inhibitory rate of B to CYP-2C9 was more than 50% at a concentration of 10M, showing a potential drug-drug interaction risk; whereas R configuration compound B1 had a 26% inhibition rate to CYP-2C9 at a concentration of 10M, showing good safety performance.

Example 5

In this example, R configuration compound B1 obtained in Example 1, the corresponding racemic compound B and the demethyl analogue A-55 disclosed in patent WO2014113191A1 were subjected to drug metabolism assay to test the pharmacokinetic properties of these drugs.

Specific Experiment Procedure:

Male Spraguee-Dawley rats (body weight: 220 g~250 g) were purchased from Slac Laboratory Animals (Shanghai). The concentration of all compounds was 1 mg/mL; intravenous administration was by tail injection at a dose of 1 mL/kg; oral dose was 10 mL/kg. Blood samples were taken through the posterior orbital vein and the blood samples were placed in a tube containing EDTA (as an anticoagulant) and stored in a −80° C. environment after centrifugation with a refrigerated centrifuge. Blood sample (at an amount of folds of 25 μL) was taken and cold acetonitrile containing the internal standard (100 μL) was added. Sample was centrifuged for 10 minutes to precipitate the plasma protein. Finally, supernatant (10 μL) was injected into the LC-MS/MS system for analysis.

LC-MS/MS analysis method: All samples were analyzed by LC-MS/MS system of API4000 QTRAP mass spectrometer equipped with LC-20AD and CBM-20A controllers, DGU-20A solvent degasser and SIL-20A autosampler (Japan Shimadzu, Colombia, Md., USA). A Bona Aeger Venusil XBP C18 column (50×2.1 mm; filler 5 micron particle size) was used for HPLC separation. The column temperature was maintained at 40° C. The flow rate was 0.3 mL/min and the total run time was 6 minutes.

For the quantification of MS/MS, the API4000 QTRAP mass spectrometer was operated in an ESI positive mode with multiple reaction monitoring (MRM). All compounds and internal standards were set to be monitored during a residence time of 100 milliseconds. The other MS/MS parameters were set as follows: atomization gas (GS1) at 30 psi, 55 lb turbine pressure, 4500V ion spray voltage, 500° C. ion source temperature. For the selected ion transitions, each analyte was tested at the optimal sensitivity of the cluster potential (DP) and the collision energy (CE). Finally, the data was collected and processed using AB SCIEX Analysist 1.5.2 data collection and integration software.

Figure 5:
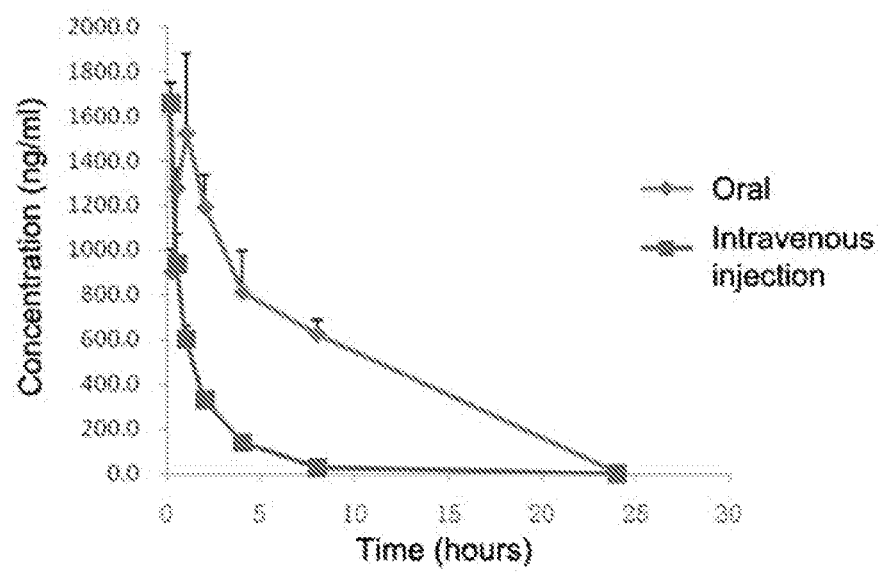
FIG. 5 is a graph showing the pharmacokinetic profile of compound B1 in Example 5.
Figure 6:
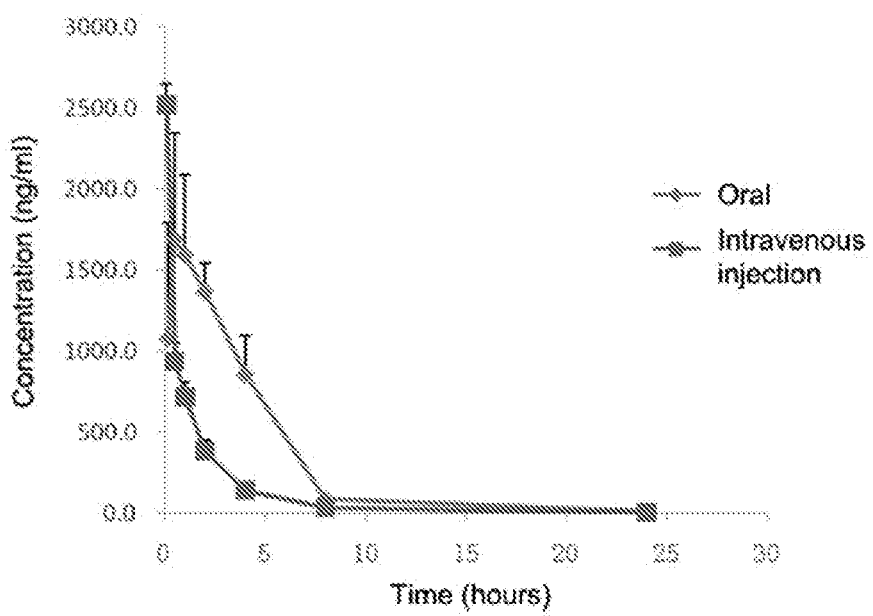
FIG. 6 is a graph showing the pharmacokinetic profile of compound B in Example 5.

Results of experiments were shown in Table 3, FIG. 5 and FIG. 6:

was nearly doubled; the half-life was increased; and the drug exposure (area under the curve AUC) was significantly increased. Thus, the pharmacokinetic assay results demonstrated that the R configuration compound B1 can inhibit the Hh signaling pathway better and more consistently than the demethyl analogue and the racemic compound, and thus has a better therapeutic application prospect for diseases associated with Hh signaling pathway.

Example 6

In this example, R configuration compound B1 obtained in Example 1 and the corresponding racemic compound B were investigated in mouse tumor model to test the inhibitory effect of R configuration compound B1 and racemic compound B on tumors related to Hh pathway.

Specific Experiment Procedure:

Tumor cells from the primary medulloblastoma of Patched (PTCH)+/−, p53−/− mice were injected subcutaneously into the right side of SCID mice. About 7 days after implantation, treatments were started when the tumor volume grew to an average of 200 mm$^3$. Animals were randomly divided into blank group, compound B administration

TABLE 3

| | Compound | | | | | |
|---|---|---|---|---|---|---|
| | Racemic compound B | | B1 | | A-55 | |
| | Mode of administration | | | | | |
| | Intravenous injection | Oral | Intravenous injection | Oral | Intravenous injection | Oral |
| Dose (mg/kg) | 2 | 10 | 2 | 10 | 2 | 10 |
| Area under the curve AUC$_{0-24\,h}$(ng · h/mL) | 2905 | 7685 | 2233 | 12324 | 1780 | 5540 |
| Clearance CL (mL · min$^{-1}$ · kg$^{-1}$) | 11.4 | | 14.4 | | 18.6 | |
| Apparent volume of distribution V$_{d,\,ss}$(L/kg) | 3.1 | | 2.2 | | 1.7 | |
| Maximum plasma concentration C$_{max}$(ng/mL) | | 1687 | | 1520 | | 2180 |
| Peak time T$_{max}$(h) | | 0.5 | | 1 | | 0.5 |
| Half-life t$_{1/2}$(h) | | 1.7 | | 1 | | |
| Bioavailability F % | | 53 | | 100 | | 62 |

Figure 7:
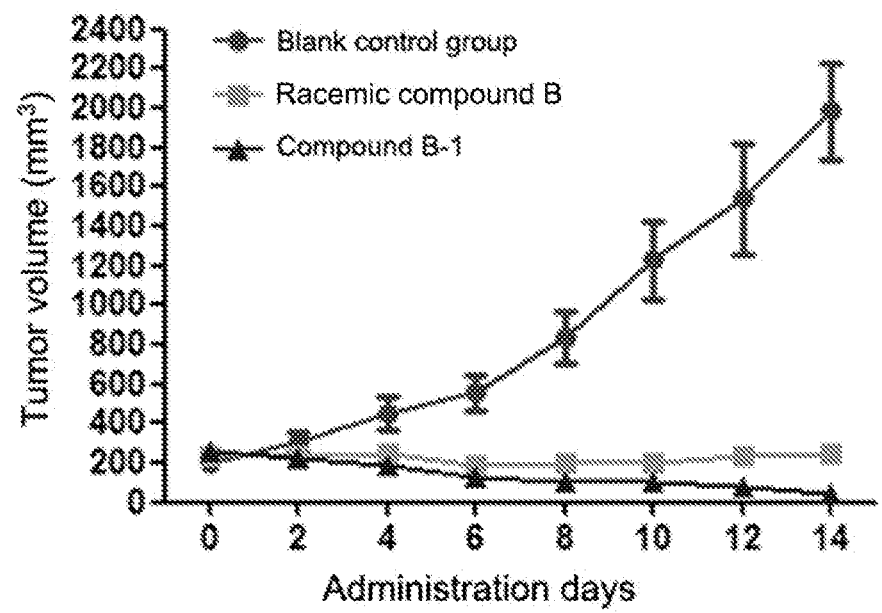
FIG. 7 is a graph showing the comparison of tumor volume inhibition in Example 6.
Figure 8:
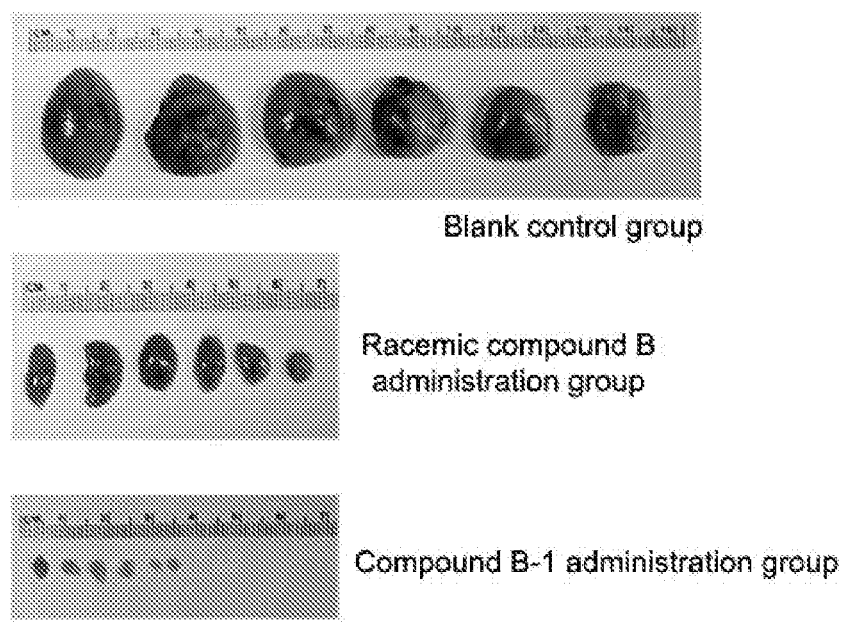
FIG. 8 is picture showing the comparison of tumor volume inhibition in Example 6.
Figure 9:
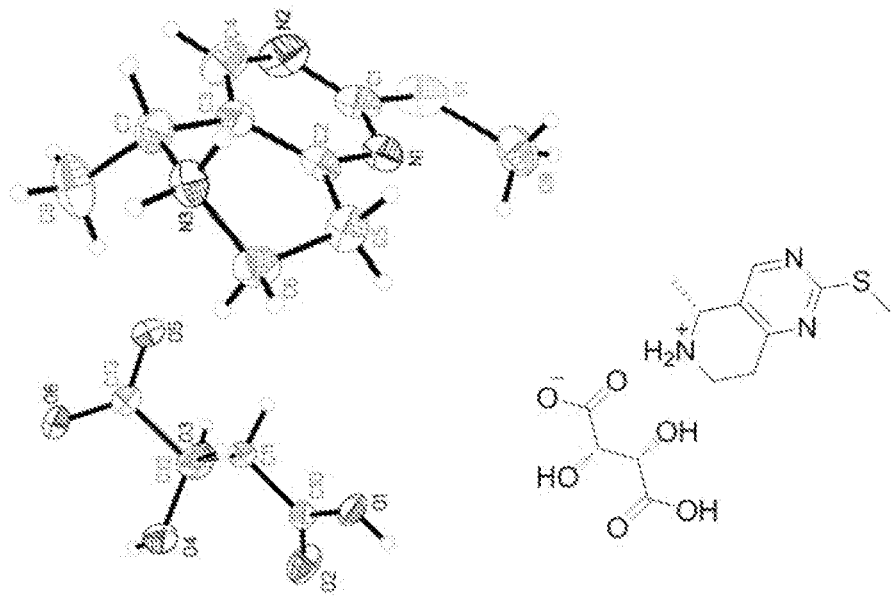
FIG. 9 is the structure of the D-tartrate salt of intermediate B1-3 in Example 7, determined by single crystal diffraction.

The results show that compared with racemic compound B, the area under the curve of R configuration compound B1 was nearly doubled and the bioavailability was increased from 53% to 100%. This experimental data demonstrated that the absorption rate of R configuration compound B1 was higher than that of racemic compound B in the animal. At the same dose, the plasma concentration of R configuration compound B1 was sustained more stable and longer in the animal. When the oral dose was 10 mg/kg, R configuration compound B1 has a plasma concentration of 623 ng/mL after 8 hours, 1340 nM in terms of molecular weight conversion, that was 1675 times of its IC50 (0.8 nM), and after the deduction of plasma protein binding, it still can inhibit Hh pathway greatly. Whereas the racemic compound B has a plasma concentration of 83 ng/mL after 8 hours, 178 nM in terms of molecular weight conversion, that was 66 times of its IC$_{50}$ (2.7 nM), and then deduct the binding of plasma protein, there was not enough plasma concentration to inhibit the Hh pathway. Compared with the demethyl analogue A-55, the bioavailability of chiral compound B1 group and compound B1 administration group. The doses of compound B1 and racemic compound B were 100 mg/kg/day. Tumor volume (m$^3$) and body weight (g) were recorded every other day. After 14 days of administration, mice were sacrificed and the tumors were removed. The results were shown in FIGS. 7 and 8.

At a dose of 100 mg/kg, the racemic compound B only stopped the growth of tumor, whereas the B1 can reduce the tumor volume to almost disappear. This result demonstrated that R configuration compound B has a more prominent and unexpected anti-tumor effect.

As can be seen from the above examples, the chiral compound B1 of Example 1 in the present disclosure was able to block the Hedgehog pathway, thereby suppressing abnormal cell growth and blocking metastasis and regeneration of tumor cells. Compared with racemic compound B, the chiral compound B1 has a better activity to inhibit the Hh pathway, better safety, and better bioavailability. In the living body, the chiral compound B1 has a more prominent, unexpected effect on inhibiting abnormal cell growth and blocking metastasis and regeneration of tumor cells, with a better application prospect of tumor treatment.

SYNTHESIS

Example 7: Preparation of (R)-1-(6-(5'-chloro-3,5-dimethyl-[2,4'-bipyridin]-2'-yl)-5-methyl-5,6,7,8-tetrahydropyrido[4,3-d]pyrimidin-2-yl)piperidin-4-ol (B1)

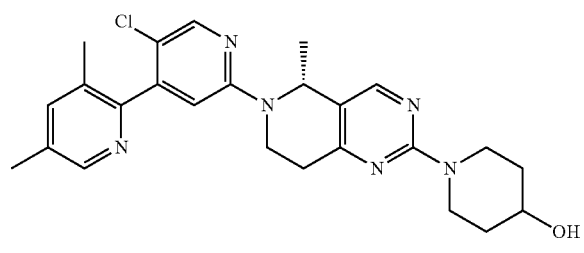

Synthetic Route A:

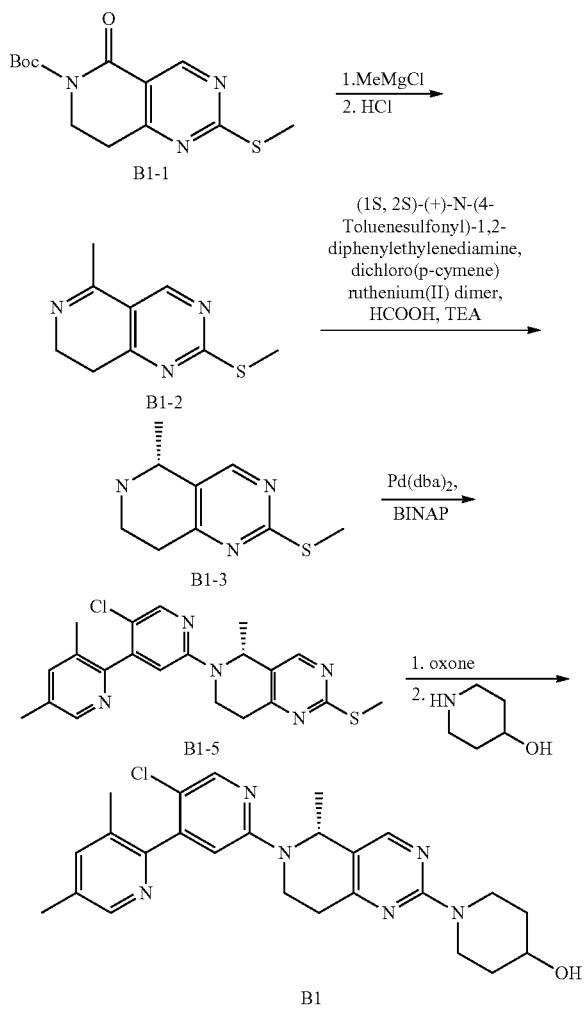

5-Methyl-2-(methylthio)-7,8-dihydropyrido[4,3-d]pyrimidine (B1-2)

Methylmagnesium chloride (3.0 M in THF, 5.3 mL, 15.9 mmol) was added dropwise to a solution of tert-butyl 2-(methylthio)-5-oxo-7,8-dihydropyrido[4,3-d]pyrimidine-6(5H)-carboxylate (compound B1-1, 4.3 g, 14.576 mmol) in THF (40 mL) under $N_2$ atmosphere at −60° C. After being stirred for 2 h at the same temperature, the reaction mixture was quenched with brine (30 mL). The resulting mixture was filtered, and the filtrate was extracted with EtOAc (30 mL×3). The combined organic layers were dried over $Na_2SO_4$, and filtered. The filtrate was concentrated under reduced pressure. The residue was dissolved in 20 mL of $CH_2Cl_2$, and TFA (10 mL) was added. The mixture was stirred at room temperature for 5 h and concentrated under reduced pressure. The residue was adjusted to pH 8-9 by adding saturated aqueous $NaHCO_3$ and extracted with $CH_2Cl_2$ (30 mL×3). The combined organic layers were dried over $Na_2SO_4$, and filtered. After removal of the solvent, the residue was purified by silica gel column chromatography (petroleum ether/EtOAc v:v=1/3) to give the title compound as a yellow solid (1.7 g, 60%). 1H NMR (400 MHz, $CDCl_3$) δ 8.50 (s, 1H), 3.85 (t, J=6.8 Hz, 2H), 2.82 (t, J=7.2 Hz, 2H), 2.60 (s, 3H), 2.37 (s, 3H).

(R)-5-Methyl-2-(methylthio)-5,6,7,8-tetrahydropyrido[4,3-d]pyrimidine (B1-3)

(1S, 2S)-(+)-N-(4-Toluenesulfonyl)-1,2-diphenylethylenediamine (209 mg, 0.571 mmol) and dichloro(p-cymene)ruthenium(II) dimer (174 mg, 0.284 mmol) were charged into a round-bottom flask (250 mL). Then a solution of TEA (2.3 g, 22.772 mmol) and formic acid (2.6 g, 56.522 mmol) in ACE (20 mL) was added under $N_2$ atmosphere, the mixture was stirred at room temperature for 10 min. A solution of 5-methyl-2-(methylthio)-7,8-dihydropyrido[4,3-d]pyrimidine (2.2 g, 11.4 mmol) in acetonitrile (40 mL) was added, and the mixture was stirred at room temperature overnight under $N_2$ atmosphere. The reaction solution was quenched with water (10 mL) and adjusted to pH 8-9 by adding saturated aqueous $NaHCO_3$. The mixture was concentrated under reduced pressure to remove most of acetonitrile and extracted with $CH_2Cl_2$ (40 mL×5). The combined organic layers were dried over $Na_2SO_4$, and filtered. After removal of the solvent, the residue was purified by silica gel column chromatography ($CH_2Cl2$/MeOH v:v=100/1 to 50/1) to give a brown solid (1.4 g, ee=60%), which was dissolved in 20 mL of MeOH, then a solution of D-tartatic acid (1.4 g, 9.333 mmol) in MeOH (5 mL) was added at 70° C. The mixture was stirred at the same temperature for 2 h. The resulting precipitate was isolated by filtration and washed with MeOH (5 mL). The solid was added to 15 mL of MeOH, and stirred at 70° C. for 10 h. After cooling to room temperature, the suspension was filtered. The solid was added to MeOH (15 mL), and stirred at 70° C. for 10 h again. The reaction was cooled to room temperature and filtered to give a white solid (1.2 g) as a D-tartatic acid salt, which was dissolved in 10 mL of water and adjusted to pH 8-9 by adding saturated aqueous $NaHCO_3$. The aqueous solution was extracted with $CH_2Cl_2$ (30 mL×5). The combined organic layers were dried over $Na_2SO_4$, and filtered. The filtrate was concentrated under reduced pressure to give the title compound (483 mg, 22%) as a white solid. $[\alpha]_D^{28}$=+64.8 (c=0.5, $CHCl_3$). 1H NMR (400 MHz, $CDCl_3$) δ 8.29 (s, 1H), 4.14 (q, J=6.7 Hz, 1H), 3.42-3.35 (m, 1H), 3.15-3.09 (m, 1H), 3.01-2.93 (m, 1H), 2.87-2.80 (m, 1H), 2.55 (s, 3H), 1.51 (d, J=6.4 Hz, 3H).

(R)-6-(5'-Chloro-3,5-dimethyl-[2,4'-bipyridin]-2'-yl)-5-methyl-2-(methylthio)-5,6,7,8-tetrahydropyrido[4,3-d]pyrimidine (B1-5)

A mixture of (R)-5-methyl-2-(methylthio)-5,6,7,8-tetrahydropyrido[4,3-d]pyrimidine (130 mg, 0.67 mmol), 2',5'-dichloro-3,5-dimethyl-2,4'-bipyridine (B1-4, 168 mg, 0.0.67 mmol), sodium tert-butoxide (128 mg, 1.33 mmol), Pd(dba)$_2$ (38 mg, 0.07 mmol) and BINAP (42 mg, 0.07 mmol) in toluene (10 mL) was reacted under N$_2$ atmosphere at 120° C. overnight. After cooling to room temperature, the reaction mixture was filtered and washed with CH$_2$Cl$_2$ (20 mL). The filtrate was concentrated under reduced pressure, and the residue was purified by silica gel column chromatography (petroleum ether/EtOAc v:v=5/1) to give the title compound as a yellow oil (50 mg, 18%). $[\alpha]_D^{26}=-88.4$ (c=0.5, CHCl$_3$).

(R)-1-(6-(5'-Chloro-3,5-dimethyl-[2,4'-bipyridin]-2'-yl)-5-methyl-5,6,7,8-tetrahydropyrido[4,3-d]pyrimidin-2-yl)piperidin-4-ol (B1)

To a 10 mL of sealed tube was added (R)-6-(5'-Chloro-3,5-dimethyl-[2,4'-bipyridin]-2'-yl)-5-methyl-2-(methylthio)-5,6,7,8-tetrahydropyrido[4,3-d]pyrimidine (compound B1-5, 50 mg, 0.12 mmol) and t-BuOH (5 mL). A solution of oxone (93 mg, 0.30 mmol) in H$_2$O (1 mL) was slowly added at room temperature and allowed to stir for 5 h. Then 4-hydroxypiperidine (61 mg, 0.61 mmol) was added to the reaction solution, and the mixture was stirred at 90° C. for 36 h. After removal of the solvent, the residue was quenched with brine (20 mL) and extracted with EtOAc (20 mL×3). The combined organic layers were dried over Na$_2$SO$_4$, and filtered. After removal of the solvent, the residue was purified by silica gel column chromatography (petroleum ether/EtOAc v:v=1/1) to give the title compound as a yellow solid (15 mg, 26%). $[\alpha]_D^{26}=-50.0$ (c=0.5, CHCl$_3$); ee=97%. $^1$H NMR (400 MHz, CDCl$_3$) δ 8.35 (s, 1H), 8.21 (s, 1H), 8.10 (s, 1H), 7.43 (s, 1H), 6.60 (s, 1H), 5.40-5.31 (m, 1H), 4.47-4.31 (m, 3H), 3.98-3.88 (m, 1H), 3.45-3.36 (m, 1H), 3.30-3.24 (m, 2H), 2.93-2.85 (m, 1H), 2.78-2.72 (m, 1H) 2.38 (s, 3H), 2.18 (s, 3H), 2.00-1.90 (m, 2H), 1.54-1.50 (m, 2H), 1.42 (d, J=6.8 Hz, 3H). $^{13}$C NMR (150 MHz, CDCl$_3$) δ 163.88, 160.53, 156.40, 155.92, 152.88, 148.39, 147.38, 147.36, 138.72, 133.15, 131.36, 120.37, 118.37, 107.51, 68.44, 48.28, 41.63, 37.43, 34.33, 31.82, 20.44, 18.62, 18.25. HRMS (ESI): calcd for C25H29ClN6O [M+H]$^+$ 465.2164, found 465.2166.

Example 8: Preparation of (S)-1-(6-(5'-chloro-3,5-dimethyl-[2,4'-bipyridin]-2'-yl)-5-methyl-5,6,7,8-tetrahydropyrido[4,3-d]pyrimidin-2-yl)piperidin-4-ol (B2)

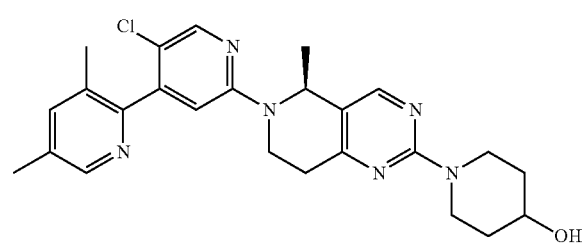

B2

Synthetic Route B:

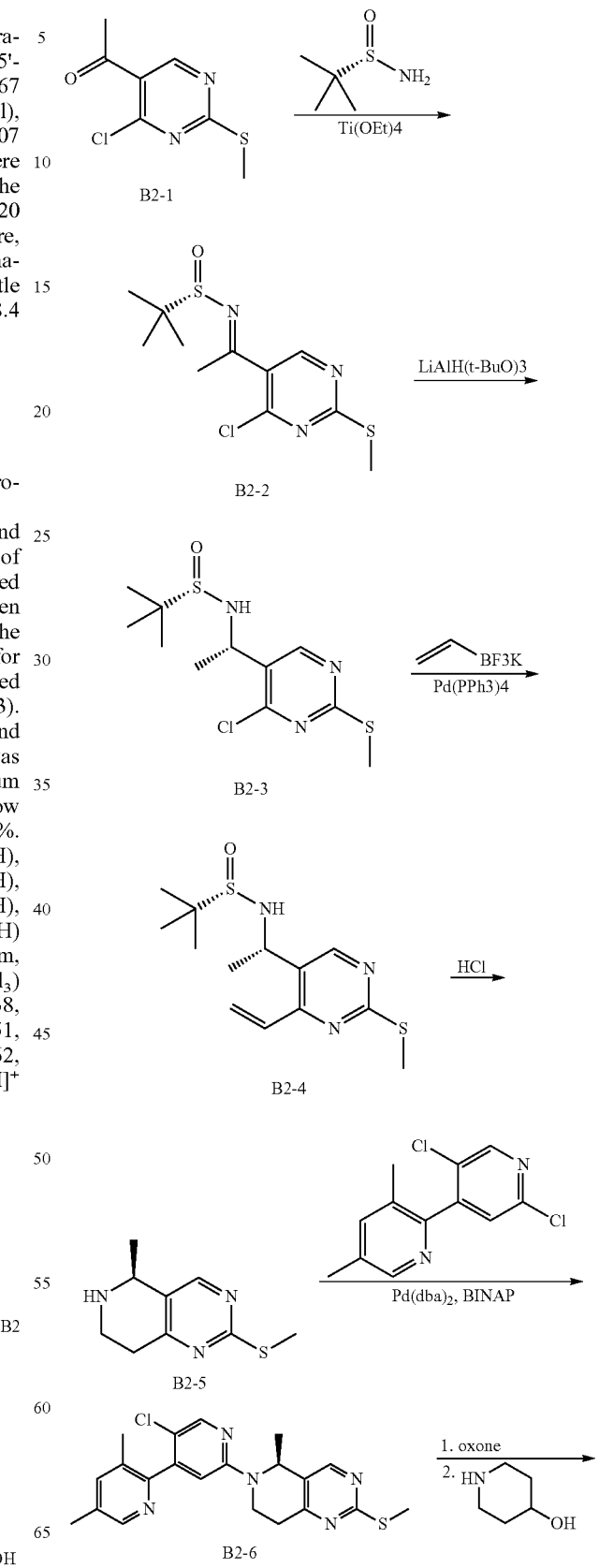

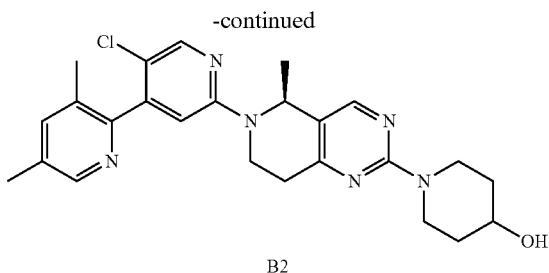

B2

(S,E)-N-(1-(4-Chloro-2-(methylthio)pyrimidin-5-yl) ethylidene)-2-methylpropane-2-sulfinamide (B2-2)

A mixture of 1-(4-chloro-2-(methylthio)pyrimidin-5-yl) ethan-1-one (compound B2-1, 1.8 g, 8.87 mmol), Ti(OEt)$_4$ (6 g, 26.32 mmol) and (S)-(−)-2-methyl-2-propanesulfinamide (2.14 g, 17.69 mmol) in dioxane (40 mL) was reacted under N$_2$ atmosphere at 90° C. for 2 h. The reaction was cooled to room temperature and concentrated under reduced pressure. To the residue was added 150 mL of ethyl acetate (EtOAc), and then H$_2$O (1 mL) was added while stirring. The resulting mixture was stirred at room temperature for 0.5 h, and then filtered. The filtrate was dried over Na$_2$SO$_4$, and filtered. After removal of the solvent, the residue was purified by silica gel column chromatography (petroleum ether/EtOAc, v:v=3/1) to give the title compound as a red oil (1.9 g, 70%). $^1$H NMR (400 MHz, CDCl$_3$) δ 8.51 (s, 1H), 2.76 (s, 3H), 2.60 (s, 3H), 1.31 (s, 9H).

(S)—N—((S)-1-(4-Chloro-2-(methylthio)pyrimidin-5-yl)ethyl)-2-methylpropane-2-sulfinamide (B2-3)

To a solution of (S,E)-N-(1-(4-chloro-2-(methylthio)pyrimidin-5-yl)ethylidene)-2-methylpropane-2-sulfinamide (500 mg, 1.63 mmol) in 25 mL of dried THF was added LiAlH[OC(CH$_3$)$_3$]$_3$ (1.24 g, 4.9 mmol) in portions at 0° C., and the mixture was stirred at the same temperature for 40 min. The mixture was treated with H$_2$O (1 mL), and concentrated under reduced pressure to remove most of THF. To the residue was added EtOAc (40 mL), and the mixture was stirred at room temperature for 0.5 h. The resulting suspension was filtered. The filtrate was dried over Na$_2$SO$_4$, and filtered. After removal of the solvent, the residue was purified by silica gel column chromatography (petroleum ether/EtOAc v:v=5/1) to give the title compound as a yellow oil (220 mg, 43%). $[α]_D^{27}$=+19.2 (c 0.5, CHCl$_3$). 1H NMR (400 MHz, CDCl$_3$) δ 8.54 (s, 1H), 4.85-4.78 (m, 1H), 3.77 (s, 1H), 2.56 (s, 3H), 1.58 (d, J=6.4 Hz, 3H), 1.24 (s, 9H).

(S)-2-Methyl-N—((S)-1-(2-(methylthio)-4-vinylpyrimidin-5-yl)ethyl)propane-2-sulfinamide (B2-4)

A mixture of (S)—N—((S)-1-(4-chloro-2-(methylthio) pyrimidin-5-yl)ethyl)-2-methylpropane-2-sulfinamide (110 mg, 0.36 mmol), potassium vinyltrifluoroborate (72 mg, 0.54 mmol), Pd(PPh$_3$)$_4$ (21 mg, 0.018 mmol) and CsF (108 mg, 0.71 mmol) in a mixed of dioxane (10 mL) and water (2 mL) was reacted under N$_2$ atmosphere at 105° C. for 2 h. The reaction was cooled to room temperature and concentrated under reduced pressure to remove dioxane. The residue was diluted with EtOAc (40 mL) and washed with brine (20 mL). The organic layer was dried over Na$_2$SO$_4$, and filtered. After removal of the solvent, the residue was purified by silica gel column chromatography (petroleum ether/EtOAc v:v=5/1) to give the title compound as a yellow oil (100 mg, 93%). $[α]_D^{27}$=+12.0 (c 0.5, CHCl$_3$). 1H NMR (400 MHz, CDCl$_3$) δ 8.55 (s, 1H), 7.08-7.01 (m, 1H), 6.71 (d, J=16.8 Hz, 1H), 5.72 (d, J=10.4 Hz, 1H), 4.85-4.73 (m, 1H), 3.45 (s, 1H), 2.58 (s, 3H), 1.56 (d, J=6.4 Hz, 3H), 1.22 (s, 9H).

(S)-5-Methyl-2-(methylthio)-5,6,7,8-tetrahydropyrido[4,3-d]pyrimidine (B2-5)

To a solution of (S)-2-methyl-N—((S)-1-(2-(methylthio)-4-vinylpyrimidin-5-yl)ethyl)propane-2-sulfinamide (330 mg, 1.1 mmol) in EtOAc (4 mL) was added 2N HCl (4 mmol) in EtOAc (2 mL). The mixture was stirred at room temperature for 5 h and concentrated under reduced pressure. The residue was dissolved in water (10 mL), then K$_2$CO$_3$ (305 mg, 2.2 mmol) and KI (183 mg, 1.1 mmol) were added. The mixture was stirred at 100° C. overnight. After cooling to room temperature, the reaction was filtered. The filtrate was extracted with CH$_2$Cl$_2$ (20 mL*4). The combined organic layers were dried over Na$_2$SO$_4$, and filtered. The filtrate was evaporated to give the title compound as a yellow oil (88 mg, 0.451 mmol, 40%). $[α]_D^{25}$=−48.0 (c 0.5, CHCl$_3$). $^1$H NMR (400 MHz, CDCl$_3$) δ 8.30 (s, 1H), 4.20-4.13 (m, 1H), 3.44-3.37 (m, 1H), 3.18-3.10 (m, 1H), 3.04-2.96 (m, 1H), 2.91-2.82 (m, 1H), 2.55 (s, 3H), 1.53 (d, J=6.4 Hz, 3H).

(S)-6-(5'-Chloro-3,5-dimethyl-[2,4'-bipyridin]-2'-yl)-5-methyl-2-(methylthio)-5,6,7,8-tetrahydropyrido[4,3-d]pyrimidine (B2-6)

A mixture of (S)-5-methyl-2-(methylthio)-5,6,7,8-tetrahydropyrido[4,3-d]pyrimidine (88 mg, 0.45 mmol), 2',5'-dichloro-3,5-dimethyl-2,4'-bipyridine (137 mg, 0.54 mmol), sodium tert-butoxide (86 mg, 0.9 mmol), bis(dibenzylideneacetone)palladium(0) (Pd(dba)$_2$, 26 mg, 0.045 mmol) and 2,2'-bis(diphenylphosphino)-1,1'-binaphthalene (BINAP, 28 mg, 0.045 mmol) in toluene (10 mL) was reacted under N$_2$ atmosphere at 120° C. overnight. After cooling to room temperature, the reaction mixture was filtered and washed with CH$_2$Cl$_2$ (20 mL). The filtrate was concentrated under reduced pressure, and the residue was purified by silica gel column chromatography (petroleum ether/EtOAc v:v=5/1) to give the title compound as a yellow oil (40 mg, 21%). [α]i=+88.0 (c 0.2, CHCl$_3$). $^1$H NMR (400 MHz, CDCl$_3$) δ 8.36 (s, 1H), 8.32 (s, 1H), 8.22 (s, 1H), 7.43 (s, 1H), 6.64 (s, 1H), 5.60-5.51 (m, 1H), 4.41-4.33 (m, 1H), 3.46-3.39 (m, 1H), 3.07-2.98 (m, 1H), 2.94-2.86 (m, 1H), 2.56 (s, 3H), 2.38 (s, 3H), 2.18 (s, 3H), 1.48 (d, J=6.8 Hz, 3H).

(S)-1-(6-(5'-Chloro-3,5-dimethyl-[2,4'-bipyridin]-2'-yl)-5-methyl-5,6,7,8-tetrahydropyrido[4,3-d]pyrimidin-2-yl)piperidin-4-ol (B2)

To a 10 mL of sealed tube was added (S)-6-(5'-chloro-3,5-dimethyl-[2,4'-bipyridin]-2'-yl)-5-methyl-2-(methylthio)-5,6,7,8-tetrahydropyrido[4,3-d]pyrimidine (40 mg, 0.1 mmol) and t-BuOH (5 mL). A solution of oxone (75 mg, 0.25 mmol) in H$_2$O (1 mL) was slowly added at room temperature and allowed to stir for 5 h. Then 4-hydroxypiperidine (40 mg, 0.4 mmol) was added to the reaction solution, and the mixture was stirred at 90° C. overnight. After removal of the solvent, the residue was quenched with brine (20 mL) and extracted with EtOAc (20 mL×3). The combined organic layers were dried over Na$_2$SO$_4$, and filtered. After removal of the solvent, the residue was purified by silica gel column chromatography (petroleum ether/EtOAc v:v=1/1) to give the title compound as a yellow solid (11 mg, 24%). $[\alpha]_D^{27}$=+54.0 (c 0.2, CHCl$_3$); ee>99%. $^1$H NMR (400 MHz, CDCl$_3$) δ 8.35 (s, 1H), 8.21 (s, 1H), 8.10 (s, 1H), 7.42 (s, 1H), 6.61 (s, 1H), 5.40-5.31 (m, 1H), 4.50-4.29 (m, 3H), 3.99-3.87 (m, 1H), 3.50-3.36 (m, 1H), 3.32-3.21 (m, 2H), 2.96-2.84 (m, 1H), 2.79-2.70 (m, 1H), 2.37 (s, 3H), 2.18 (s, 3H), 1.99-1.90 (m, 2H), 1.54-1.48 (m, 2H), 1.43 (s, 3H). $^{13}$C NMR (150 MHz, CDCl$_3$) δ 163.88, 160.53, 156.40, 155.92, 152.85, 148.37, 147.36, 138.73, 133.16, 131.37, 120.37, 118.36, 107.52, 68.43, 48.28, 41.63, 37.43, 34.32, 31.81, 20.43, 18.61, 18.24. HRMS (ESI): calcd for C$_{25}$H$_{29}$ClN$_6$O [M+H]$^+$465.2164, found 465.2165.

Example 9: Preparation of (5 S)-6-[5-chloro-4-(3,5-dimethyl-2-pyridyl)-2-pyridyl]-N-cyclopropyl-5-methyl-7,8-dihydro-5H-pyrido[4,3-d]pyrimidin-2-amine (B3)

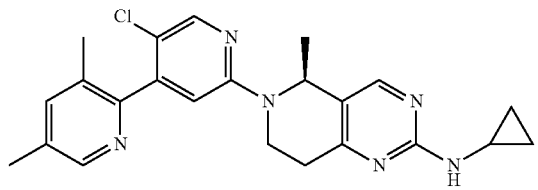

B3

Synthetic Route C:

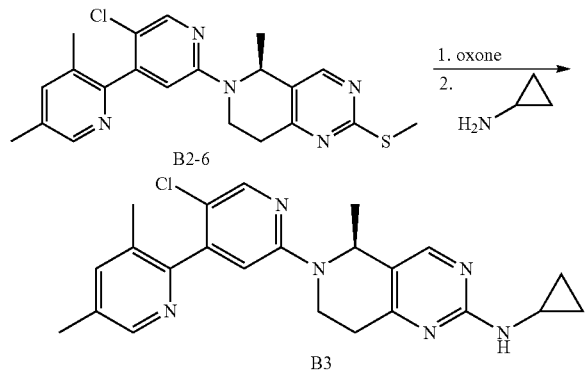

(S)-6-(5'-Chloro-3,5-dimethyl-[2,4'-bipyridin]-2'-yl)-N-cyclopropyl-5-methyl-5,6,7,8-tetrahydropyrido[4,3-d]pyrimidin-2-amine (60)

To a 10 mL of sealed tube was added (S)-6-(5'-chloro-3,5-dimethyl-[2,4'-bipyridin]-2'-yl)-5-methyl-2-(methylthio)-5,6,7,8-tetrahydropyrido[4,3-d]pyrimidine (compound B2-6, 40 mg, 0.1 mmol) and t-BuOH (5 mL). A solution of oxone (75 mg, 0.25 mmol) in H$_2$O (1 mL) was slowly added at room temperature and allowed to stir for 5 h. Then cyclopropylamine (57 mg, 1.0 mmol) was added to the reaction solution, and the mixture was stirred at 90° C. for 36 h. After removal of the solvent, the residue was quenched with brine (20 mL) and extracted with EtOAc (20 mL×3). The combined organic layers were dried over Na$_2$SO$_4$, and filtered. After removal of the solvent, the residue was purified by silica gel column chromatography (petroleum ether/EtOAc v:v=2/1 to 1/1) to give the title compound as a yellow solid (14 mg, 34%). $[\alpha]_D^{22}$=+86.0 (c 0.2, CHCl$_3$); ee>99%. $^1$H NMR (400 MHz, CDCl$_3$) δ 8.36 (s, 1H), 8.21 (s, 1H), 8.17 (s, 1H), 7.43 (s, 1H), 6.61 (s, 1H), 5.45-5.36 (m, 1H), 5.26 (s, 1H), 4.43-4.31 (m, 1H), 3.46-3.36 (m, 1H), 2.96-2.86 (m, 1H), 2.80-2.71 (m, 2H), 2.38 (s, 3H), 2.18 (s, 3H), 1.44 (d, J=5.6 Hz, 3H), 0.84-0.79 (m, 2H), 0.57-0.50 (m, 2H).

Example 10: (R)-6-(5'-Chloro-3,5-dimethyl-[2,4'-bipyridin]-2'-yl)-N-cyclopropyl-5-methyl-5,6,7,8-tetrahydropyrido[4,3-d]pyrimidin-2-amine (B4)

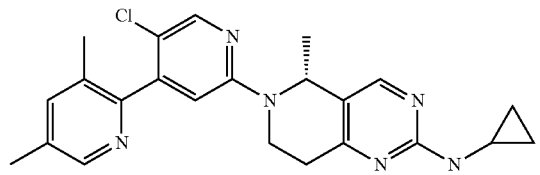

B4

Synthetic Route D:

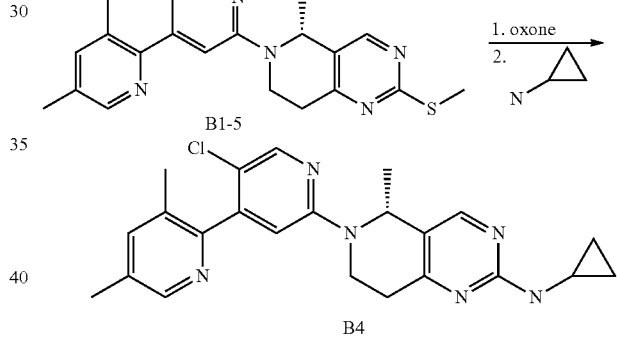

(R)-6-(5'-Chloro-3,5-dimethyl-[2,4'-bipyridin]-2'-yl)-N-cyclopropyl-5-methyl-5,6,7,8-tetrahydropyrido[4,3-d]pyrimidin-2-amine (B4)

To a 10 mL of sealed tube was added (R)-6-(5'-Chloro-3,5-dimethyl-[2,4'-bipyridin]-2'-yl)-5-methyl-2-(methylthio)-5,6,7,8-tetrahydropyrido[4,3-d]pyrimidine (compound B1-5, 35 mg, 0.08 mmol) and t-BuOH (5 mL). A solution of oxone (65 mg, 0.21 mmol) in H$_2$O (1 mL) was slowly added at room temperature and allowed to stir for 5 h. Then cyclopropylamine (48 mg, 0.85 mmol) was added to the reaction solution, and the mixture was stirred at 90° C. for 36 h. After removal of the solvent, the residue was quenched with brine (20 mL) and extracted with EtOAc (20 mL×3). The combined organic layers were dried over Na$_2$SO$_4$, and filtered. After removal of the solvent, the residue was purified by silica gel column chromatography (petroleum ether/EtOAc=2/1 to 1/1) to give the title compound as a yellow solid (7 mg, 20%). $[\alpha]_D^{22}$=−76.4 (c 0.5, CHCl$_3$); ee=97%. $^1$H NMR (400 MHz, CDCl$_3$) δ 8.35 (s, 1H), 8.21 (s, 1H), 8.16 (s, 1H), 7.42 (s, 1H), 6.61 (s, 1H), 5.44-5.35 (m, 1H), 5.22 (s, 1H), 4.42-4.30 (m, 1H), 3.44-3.37 (m, 1H), 2.97-2.85 (m, 1H), 2.80-2.70 (m, 2H), 2.37 (s, 3H), 2.17 (s, 3H), 1.44 (d, J=6.8 Hz, 3H), 0.86-0.79 (m, 2H), 0.54-0.51 (m, 2H).

Example 11: Preparation of (R)—N-(6-(5'-chloro-3,5-dimethyl-[2,4'-bipyridin]-2'-yl)-5-methyl-5,6,7,8-tetrahydropyrido[4,3-d]pyrimidin-2-yl)propionamide (B5)

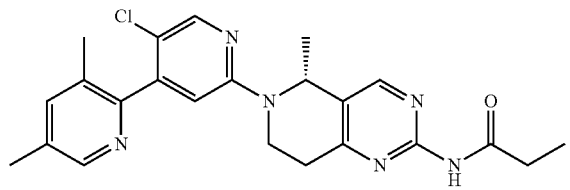

Synthetic Route E:

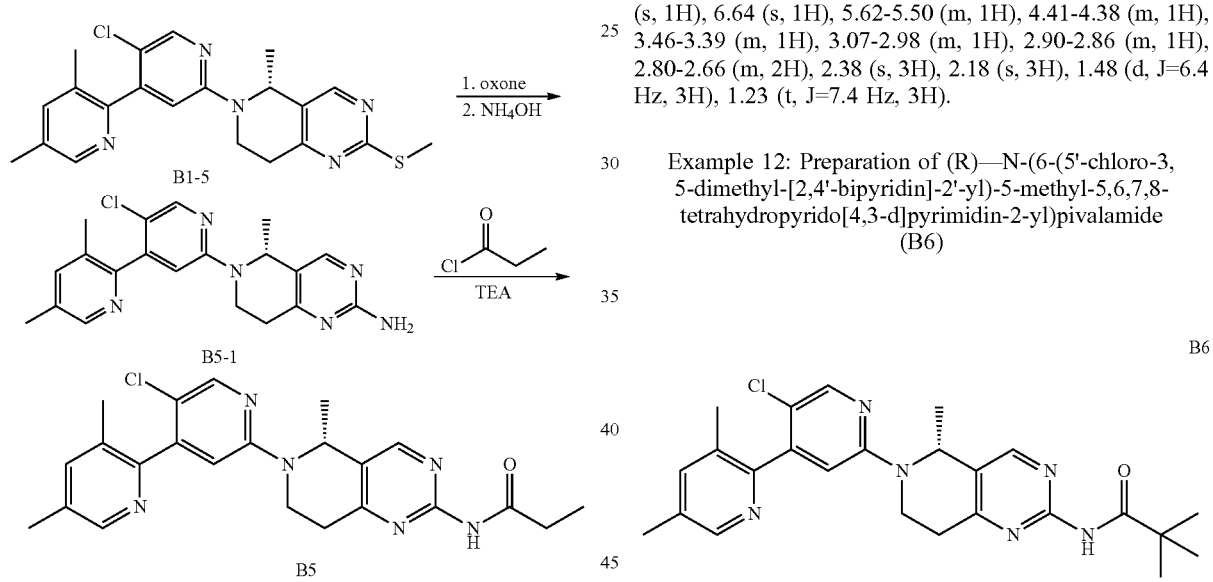

(R)-6-(5'-Chloro-3,5-dimethyl-[2,4'-bipyridin]-2'-yl)-5-methyl-5,6,7,8-tetrahydropyrido[4,3-d]pyrimidin-2-amine (B5-1)

To a 45 mL of sealed tube was added (R)-6-(5'-Chloro-3,5-dimethyl-[2,4'-bipyridin]-2'-yl)-5-methyl-2-(methylthio)-5,6,7,8-tetrahydropyrido[4,3-d]pyrimidine (compound B1-5, 550 mg, 1.3 mmol) and t-BuOH (20 mL). A solution of oxone (820 mg, 2.6 mmol) in H$_2$O (5 mL) was slowly added at room temperature and allowed to stir for 5 h. Then NH$_4$OH (25-28%, 3 mL) was added to the reaction solution, and the mixture was stirred at 90° C. for 36 h. After removal of the solvent, the residue was quenched with brine (20 mL) and extracted with EtOAc (20 mL×3). The combined organic layers were dried over Na$_2$SO$_4$, and filtered. After removal of the solvent, the residue was purified by silica gel column chromatography (petroleum ether/EtOAc v:v=1/1 to 1/2) to give the title compound as a yellow solid (200 mg, 39%).

(R)—N-(6-(5'-chloro-3,5-dimethyl-[2,4'-bipyridin]-2'-yl)-5-methyl-5,6,7,8-tetrahydropyrido[4,3-d]pyrimidin-2-yl)propionamide (B5)

To a solution of (R)-6-(5'-chloro-3,5-dimethyl-[2,4'-bipyridin]-2'-yl)-5-methyl-5,6,7,8-tetrahydropyrido[4,3-d]pyrimidin-2-amine (compound B5-1, 50 mg, 0.13 mmol) and triethylamine (141 mg, 1.4 mmol) in 10 mL of CH$_2$Cl$_2$ was added propionyl chloride (120 mg, 1.3 mmol). The mixture was stirred at room temperature for 5 h. After completion of the reaction, the mixture was treated with brine (20 mL) and extracted with CH$_2$Cl$_2$ (30 mL). The organic layer was evaporated, and the residue was dissolved in 10 mL of THF. Then NH$_4$OH (25-28%, 2 mL) was added. The resulting mixture was stirred at room temperature overnight. The reaction was diluted with brine (20 mL) and extracted with EtOAc (15 mL×3). The combined organic layers were dried over Na$_2$SO$_4$, and filtered. After removal of the solvent, the residue was purified by silica gel column chromatography (petroleum ether/EtOAc v:v=1/1) to give the title compound as a white solid (20 mg, 35%). $^1$H NMR (400 MHz, CDCl$_3$) δ 8.38 (s, 1H), 8.35 (s, 1H), 8.22 (s, 1H), 8.04 (s, 1H), 7.43 (s, 1H), 6.64 (s, 1H), 5.62-5.50 (m, 1H), 4.41-4.38 (m, 1H), 3.46-3.39 (m, 1H), 3.07-2.98 (m, 1H), 2.90-2.86 (m, 1H), 2.80-2.66 (m, 2H), 2.38 (s, 3H), 2.18 (s, 3H), 1.48 (d, J=6.4 Hz, 3H), 1.23 (t, J=7.4 Hz, 3H).

Example 12: Preparation of (R)—N-(6-(5'-chloro-3,5-dimethyl-[2,4'-bipyridin]-2'-yl)-5-methyl-5,6,7,8-tetrahydropyrido[4,3-d]pyrimidin-2-yl)pivalamide (B6)

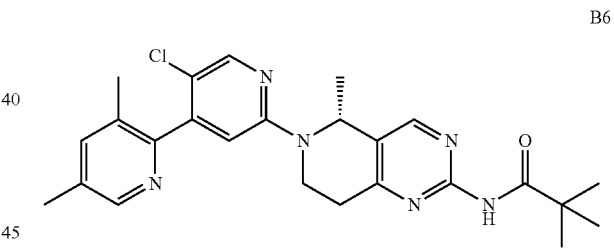

Synthetic Route F:

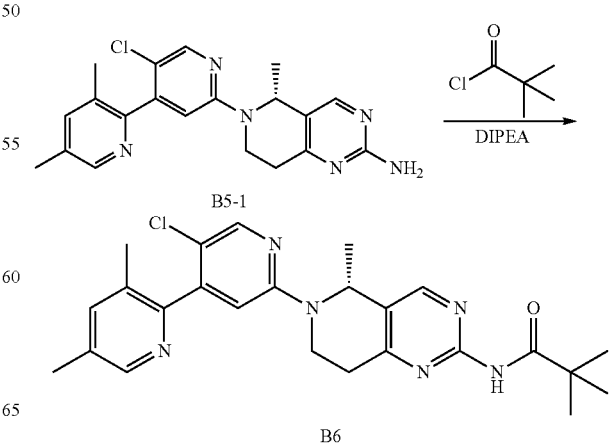

(R)—N-(6-(5'-Chloro-3,5-dimethyl-[2,4'-bipyridin]-2'-yl)-5-methyl-5,6,7,8-tetrahydropyrido[4,3-d]pyrimidin-2-yl)pivalamide (B6)

A mixture of (R)-6-(5'-chloro-3,5-dimethyl-[2,4'-bipyridin]-2'-yl)-5-methyl-5,6,7,8-tetrahydropyrido[4,3-d]pyrimidin-2-amine (100 mg, 0.26 mmol), trimethylacetyl chloride (157 mg, 1.3 mmol) and DIPEA (201 mg, 1.56 mmol) in 5 mL of dioxane was stirred at 100° C. overnight. The reaction was treated with 2M NaHCO$_3$ (20 mL) and extracted with EtOAc (20 mL×2). The combined organic layers were dried over Na$_2$SO$_4$, and filtered. After removal of the solvent, the residue was purified by silica gel column chromatography (petroleum ether/EtOAc v:v=2/1) to give the title compound as a white solid (40 mg, 32%). $^1$H NMR (400 MHz, CDCl$_3$) δ 8.41 (s, 1H), 8.35 (s, 1H), 8.22 (s, 1H), 8.03 (s, 1H), 7.43 (s, 1H), 6.63 (s, 1H), 5.65-5.43 (m, 1H), 4.47-4.27 (m, 1H), 3.48-3.30 (m, 1H), 3.09-3.01 (m, 1H), 2.94-2.86 (m, 1H), 2.37 (s, 3H), 2.18 (s, 3H), 1.47 (d, J=6.0 Hz, 3H), 1.33 (s, 9H).

Example 13: In Vitro Evaluation of Cytochrome P450 (CYP) Inhibition

Compounds B and B1 were examined in CYP inhibition assays.

CYP Inhibition Assay:

Five major CYP isozymes and their corresponding substrates are: CYP-1A2 (phenacetin, 30 μM), CYP2A6 (tolbutamide, 100 μM), CYP2C9 (tolbutamide hydroxylation), CYP2C19 (S-mephenytoin, 40 μM), CYP2D6 (dextromethorphan, 5 μM), and CYP3A4 (midazolam, 1 μM), respectively. All probe substrates were used at or lower than their KMS concentrations.

A mixture (200 μL) can be incubated at 37° C. This mixture can comprise HLM (0.2 mg/mL), phosphate buffer (100 mM, pH at about 7.4), nicotinamide adenine dinucleotide phosphate (NADPH) (1 μM), a testing compound (compound B or compound B1), and the individual substrate for the CYP isozyme tested.

Before the start of the reaction with NADPH, the above mixture can be pre-incubated for about 10 minutes to allow inhibitor-enzyme interactions. Then at specific time points (10 minutes time point for CYP-1A2, 2D6 and 3A4; 30 minutes time point for CYP-2C9 and 2C19), the reaction can be quenched by the addition of about 100 μL cold acetonitrile. The quenched mixture can be centrifuged, and aliquots of the mixture can then be analyzed by LC-MS/MS to quantify the concentrations of specific metabolic products for each CYP isozyme. For each testing compound, at least three independent assays can be completed. Results of the CYP inhibition assay can be shown in Table 6 below.

According to Table 6, compound B exhibited more than 50% inhibition of CYP-2C9 while compound B1 exhibited about 26% inhibition of CYP-2C9 at 10 M concentration.

Example 14: Pharmacokinetics Experiments of Compounds B, B1 and A-55

Compounds B, B1 and A-55 were tested in pharmacokinetics evaluations as follows.

Pharmacokinetics Experiments:

Test subjects, Sprague-Dawley rats (body weight from about 220 g to about 250 g), were purchased from Slac Laboratory Animals (Shanghai, China). All compounds tested at 1 mg/mL concentration, either intravenous injected at a tail vein at 1 mL/kg dosage for one group of test subjects or administered orally at a dose of 10 mL/kg in another group of test subjects. Then aliquots of blood samples were collected by retro-orbital venous plexus puncture at time intervals after the injection/administration. The blood samples were kept in tubes containing EDTA, centrifuged and stored at −80° C. before analysis. Blank plasma was collected by the same method before rats were treated with compounds. Plasma samples for analysis were obtained by removing about 25 μL from the saved blood sample; adding cold acetonitrile (about 100 μL) as internal standard; centrifuged for 10 minutes to precipitate plasma proteins; and collect about 10 μL of the upper clear solution for analysis done by an LC-MS/MS system.

LC-MS/MS Analysis Method:

All samples were analyzed by an API 4000 QTRAP® LC/MS/MS System equipped with Shimadzu LC-20AD pump, Shimadzu CBM-20A controller, SIL-20A autosampler and DGU-20A degasser (Shimadzu, Columbia, Md., USA). A Venusil XBP C18 HPLC Column (2.1×50 mm, 5 μm) (Bonna-Agela Technologies) was used for HPLC separation at isocratic temperature of 40° C. Flow rate was kept at 0.3 mL/min and the total run time was kept at 6 minutes.

Quantification by MS/MS is done using the above-described API 4000 QTRAP mass spectrometer equipped with multiple reaction monitoring (MRM) and positive electrospray ionization (ESI+) modes. All compounds and internal standard were detected at retention time of about 100 milliseconds. Other parameters for MS/MS are shown below: Ion Source Gas 1 (GS1) at 30 psi, turbine pressure at 55 pounds, ion spray voltage at 4500 V, and ion source temperature at 500° C. MRM measurements of the analytes were performed using declustering potential (DP) and entrance potential (EP) values optimized for each analyte. Finally, all of the operations, the acquisition and analysis of data were controlled by Analyst (version 1.5.2, AB Sciex, USA).

Figure 14:
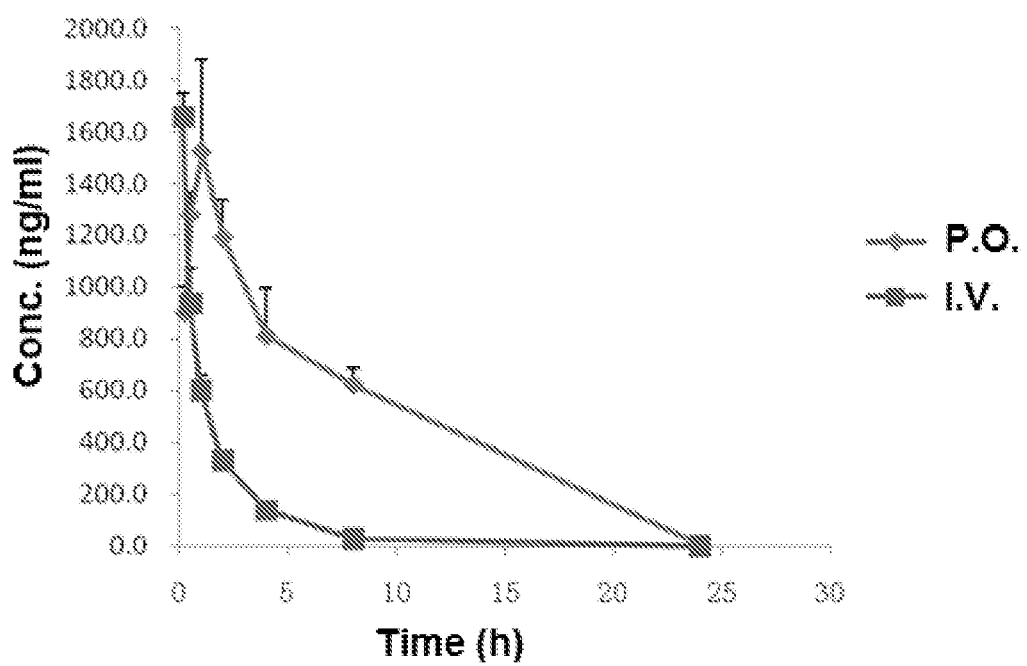
FIG. 14 shows the metabolism curve of compound B1 in Example 14 in rat.
Figure 15:
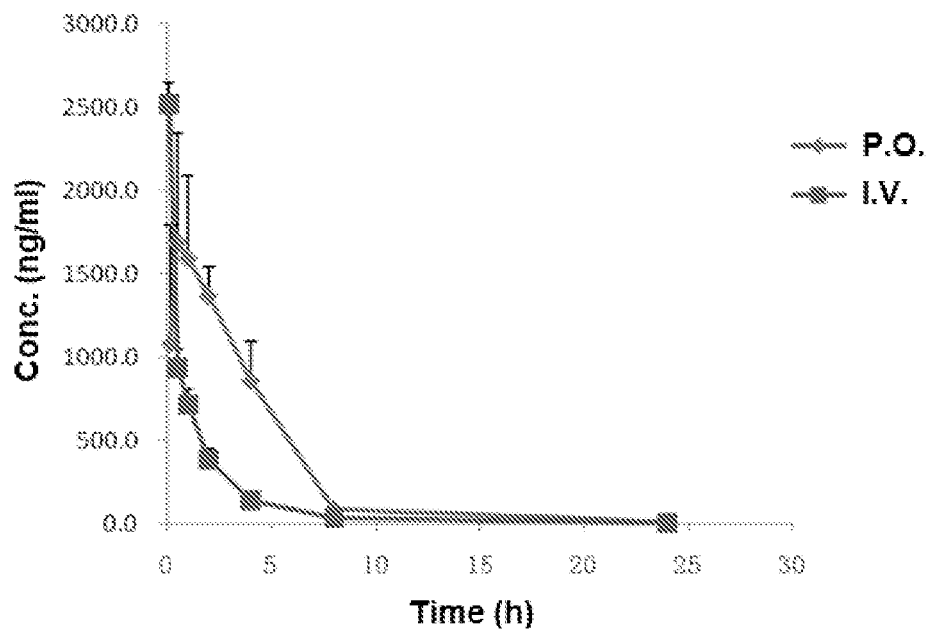
FIG. 15 shows the metabolism curve of compound B in Example 14 in rat.

Experimental results are shown in Table 7 and FIGS. 14 and 15.

TABLE 6

CYP inhibition results for compounds B and B1.

| Compd | CYP-3A4 Inhibition (%) | CYP-2D6 Inhibition (%) | CYP-1A2 Inhibition (%) | CYP-2C9 Inhibition (%) | CYP-2C19 Inhibition (%) |
|---|---|---|---|---|---|
| H$_2$O | 0.0 ± 9.7 | 0.0 ± 9.3 | 0.0 ± 7.4 | 0.0 ± 4.3 | 0.0 ± 4.4 |
| Positive Control | 96 ± 0.23 | 94 ± 1.0 | 95 ± 0.8 | 81 ± 1.4 | 58 ± 1.2 |
| B | 21 ± 4.0 | 30 ± 1.7 | 21 ± 1.3 | 52 ± 5.2 | 44 ± 3.3 |
| B1 | 20 ± 5.9 | 24 ± 3.5 | 22 ± 15 | 26 ± 6.0 | 43 ± 2.6 |

TABLE 7

Results of pharmacokinetics experiments of compounds B, B1 and A-55.

| | Compd | | | | | |
|---|---|---|---|---|---|---|
| | B | | B1 | | A-55 | |
| | Administration | | | | | |
| | I.V. | P.O. | I.V. | P.O. | I.V. | P.O. |
| Dosage (mg/kg) | 2 | 10 | 2 | 10 | 2 | 10 |
| AUC$_{0-24\,h}$(ng · h/mL) | 2905 | 7685 | 2233 | 12324 | 1780 | 5540 |

TABLE 7-continued

Results of pharmacokinetics experiments of compounds B, B1 and A-55.

| Compd | B | | B1 | | A-55 | |
|---|---|---|---|---|---|---|
| Administration | I.V. | P.O. | I.V. | P.O. | I.V. | P.O. |
| CL (mL · min$^{-1}$ · kg$^{-1}$) | 11.4 | | 14.4 | | 18.6 | |
| $V_{d, ss}$(L/kg) | 3.1 | | 2.2 | | 1.7 | |
| $C_{max}$(ng/mL) | | 1687 | | 1520 | | 2180 |
| $T_{max}$(h) | | 0.5 | | 1 | | 0.5 |
| $t_{1/2}$(h) | | | 1.7 | | 1 | |
| F % | | 53 | | 100 | | 62 |

Experimental results showed that chiral compound B1 can be superior to the racemic compound B in AUC (almost doubled) and bioavailability (increased from 53% to about 100%) measurements. In addition, chiral compound B1 can have higher absorption rate in animals than racemic compound B. Chiral compound B1 also can have more stable plasma levels and longer durations when compared with racemic compound B. For p.o. dosage at 10 mg/kg, chiral compound B1 can maintain a plasma concentration of 623 ng/mL at the 8-hour time point, which can be about 1340 nM, about 1675 folds of its IC$_{50}$ value (0.8 nM). Even considering absorption by plasma proteins, chiral compound B1 can achieve its desired inhibition of hedgehog signaling. In contrast, racemic compound B can have a plasma concentration of 83 ng/mL at the 8-hour time point, or about 178 nM, about 66 folds of its IC$_{50}$ value (2.7 nM).

Experimental results also showed that compared desmethyl compound A-55, chiral compound B1 can increase its bioavailabilty (100% for B1 vs. 62% for A-55), longer half-life in animal bodies, better drug exposure (AUS of B1 increases by 122% over that of A-55).

Overall, experimental results showed that compared with desmethyl compound A-55 and racemic compound B, chiral compound B1 may inhibit Hh signaling pathway better and longer, thereby it may enjoy better application in treating diseases associated with Hh signaling pathway.

Example 15: Inhibition of Tumors in Mouse

Compounds B and B1 were tested in tumor inhibition studies in mice as follows.

Figure 16:
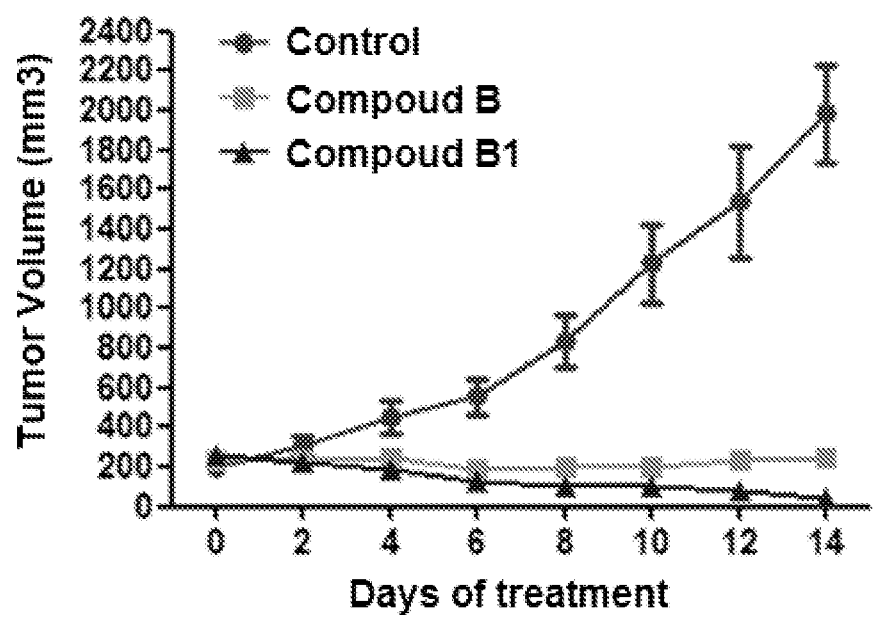
FIG. 16 depicts the tumor volume over time curve for tumor in Example 15.
Figure 17:
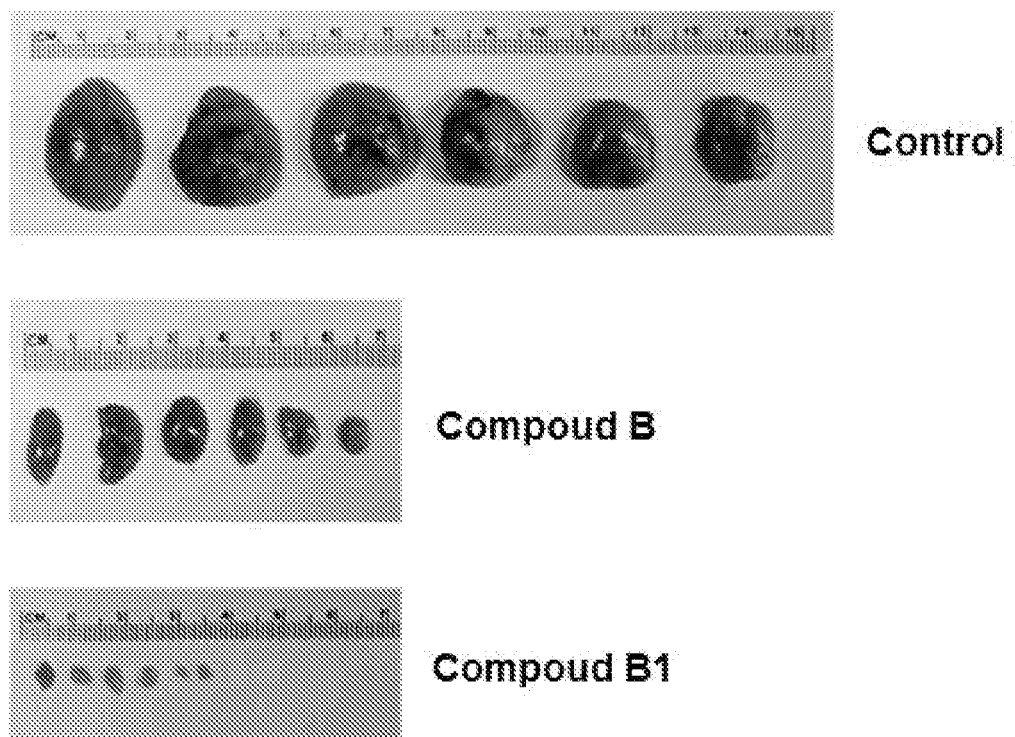
FIG. 17 depicts the photos of tumors at different time points in Example 15.

Tumor Inhibition Experiments:

Primary medulloblastoma (5×10$^6$) from Patched (PTCH)+/−, p53−/− mice can be intravenously injected into the right sides of SCID mice. Seven days after the injection, treatment with drugs can start when the average size of tumors reaches 200 mm$^3$. Subjects can be randomly assigned to the control group, the compound B-treatment group and the compound B1-treatment group. Compounds B and B1 can be administered at dosages of about 100 mg/kg/day. The tumor volume and the body weights of the subjects can be measured and recorded every other day. On the 14$^{th}$ day after the drug administration, the subjects can be sacrificed and their tumors can be removed. Results of the experiments are shown in FIGS. 16 and 17.

At a dosage of 100 mg/kg, racemic compound B may stop the tumors from growing. In contrast, at a dosage of 100 mg/kg, chiral compound B1 may decrease the tumor volume and may reduce the tumor size so drastically that the tumor can be considered removed.

Table 4 shows a selection of compounds prepared according to the disclosed methods of the present disclosure.

| Compd | Structure | NMR |
|---|---|---|
| B1 | (structure shown) | $^1$H NMR (400 MHz, CDCl$_3$) δ 8.35 (s, 1H), 8.21 (s, 1H), 8.10 (s, 1H), 7.43 (s, 1H), 6.60 (s, 1H), 5.40-5.31 (m, 1H), 4.47-4.31 (m, 3H), 3.98-3.88 (m, 1H), 3.45-3.36 (m, 1H), 3.30-3.24 (m, 2H), 2.93-2.85 (m, 1H), 2.78-2.72 (m, 1H) 2.38 (s, 3H), 2.18 (s, 3H), 2.00-1.90 (m, 2H), 1.54-1.50 (m, 2H), 1.42 (d, J = 6.8 Hz, 3H). $^{13}$C NMR (150 MHz, CDCl$_3$) δ 163.88, 160.53, 156.40, 155.92, 152.88, 148.39, 147.38, 147.36, 138.72, 133.15, 131.36, 120.37, 118.37, 107.51, 68.44, 48.28, 41.63, 37.43, 34.33, 31.82, 20.44, 18.62, 18.25. HRMS (ESI): calcd. for C25H29ClN6O [M + H]$^+$ 465.2164, found 465.2166. |
| B2 | (structure shown) | $^1$H NMR (400 MHz, CDCl$_3$) δ 8.35 (s, 1H), 8.21 (s, 1H), 8.10 (s, 1H), 7.42 (s, 1H), 6.61 (s, 1H), 5.40-5.31 (m, 1H), 4.50-4.29 (m, 3H), 3.99-3.87 (m, 1H), 3.50-3.36 (m, 1H), 3.32-3.21 (m, 2H), 2.96-2.84 (m, 1H), 2.79-2.70 (m, 1H), 2.37 (s, 3H), 2.18 (s, 3H), 1.99-1.90 (m, 2H), 1.54-1.48 (m, 2H), 1.43 (s, 3H). $^{13}$C NMR (150 MHz, CDCl$_3$) δ 163.88, 160.53, 156.40, 155.92, 152.85, 148.37, 147.36, 138.73, 133.16, 131.37, 120.37, 118.36, 107.52, 68.43, 48.28, 41.63, 37.43, 34.32, 31.81, 20.43, 18.61, 18.24. HRMS (ESI): calcd. for C$_{25}$H$_{29}$ClN$_6$O [M + H]$^+$ 465.2164, found 465.2165. |

| Compd | Structure | NMR |
|---|---|---|
| B3 | 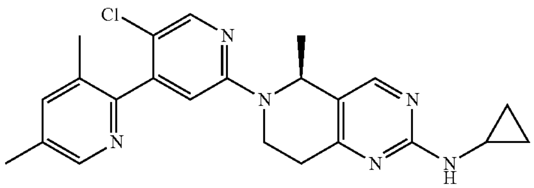 [SMILES: Cc1cnc(-c2cc(N3CCc4nc(NC5CC5)ncc4[C@@H]3C)ncc2Cl)c(C)c1] | $^1$H NMR (400 MHz, CDCl$_3$) δ 8.36 (s, 1H), 8.21 (s, 1H), 8.17 (s, 1H), 7.43 (s, 1H), 6.61 (s, 1H), 5.45-5.36 (m, 1H), 5.26 (s, 1H), 4.43-4.31 (m, 1H), 3.46-3.36 (m, 1H), 2.96-2.86 (m, 1H), 2.80-2.71 (m, 2H), 2.38 (s, 3H), 2.18 (s, 3H), 1.44 (d, J = 5.6 Hz, 3H), 0.84-0.79 (m, 2H), 0.57-0.50 (m, 2H). |
| B4 | 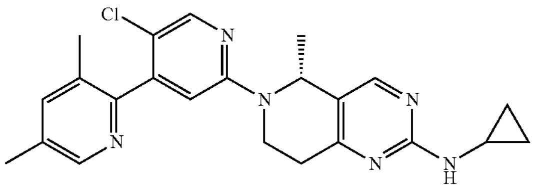 [SMILES: Cc1cnc(-c2cc(N3CCc4nc(NC5CC5)ncc4[C@H]3C)ncc2Cl)c(C)c1] | $^1$H NMR (400 MHz, CDCl$_3$) δ 8.35 (s, 1H), 8.21 (s, 1H), 8.16 (s, 1H), 7.42 (s, 1H), 6.61 (s, 1H), 5.44-5.35 (m, 1H), 5.22 (s, 1H), 4.42-4.30 (m, 1H), 3.44-3.37 (m, 1H), 2.97-2.85 (m, 1H), 2.80-2.70 (m, 2H), 2.37 (s, 3H), 2.17 (s, 3H), 1.44 (d, J = 6.8 Hz, 3H), 0.86-0.79 (m, 2H), 0.54-0.51 (m, 2H). |
| B5 | 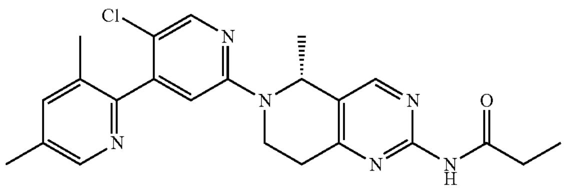 [SMILES: CCC(=O)Nc1ncc2c(n1)CCN(c1cc(-c3ncc(C)cc3C)c(Cl)cn1)[C@@H]2C] | $^1$H NMR (400 MHz, CDCl$_3$) δ 8.38 (s, 1H), 8.35 (s, 1H), 8.22 (s, 1H), 8.04 (s, 1H), 7.43 (s, 1H), 6.64 (s, 1H), 5.62-5.50 (m, 1H), 4.41-4.38 (m, 1H), 3.46-3.39 (m, 1H), 3.07-2.98 (m, 1H), 2.90-2.86 (m, 1H), 2.80-2.66 (m, 2H), 2.38 (s, 3H), 2.18 (s, 3H), 1.48 (d, J = 6.4 Hz, 3H), 1.23 (t, J= 7.4 Hz, 3H). |
| B6 | 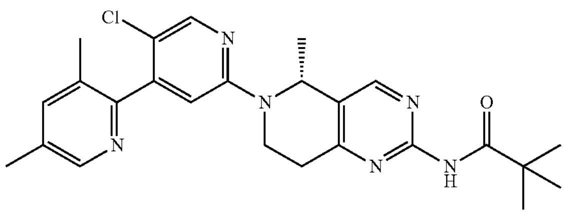 [SMILES: Cc1cnc(-c2cc(N3CCc4nc(NC(=O)C(C)(C)C)ncc4[C@H]3C)ncc2Cl)c(C)c1] | $^1$H NMR (400 MHz, CDCl$_3$) δ 8.41 (s, 1H), 8.35 (s, 1H), 8.22 (s, 1H), 8.03 (s, 1H), 7.43 (s, 1H), 6.63 (s, 1H), 5.65-5.43 (m, 1H), 4.47-4.27 (m, 1H), 3.48-3.30 (m, 1H), 3.09-3.01 (m, 1H), 2.94-2.86 (m, 1H), 2.37 (s, 3H), 2.18 (s, 3H), 1.47 (d, J = 6.0 Hz, 3H), 1.33 (s, 9H). |

Biological Activities:

The primary assay is based on NIH3T3-GRE-Luc Reporter Gene Assay:

NIH3T3 cells (CRL-1658, ATCC) were maintained in DMEM (11965, Gibico) supplemented with 10% FBS (Hyclone). GRE-Luc plasmid was generated by cloning 8×Gli-1 responsive element (GRE) into the MCS of pGL4.26 (Promega). NIH3T3-GRE-Luc reporter cell lines were established by hygromycin (Invitrogen) selection after transfection with GRE-Luc luciferase reporter plasmid. Single clones were validated for the assay quality with N-terminal fragment of recombinant sonic hedgehog protein or small molecule agonist SAG (ABIN629346). Selected clone were used to monitor the Hh signaling.

The NIH3T3-GRE-Luc cells were maintained in complete culture medium (DMEM with 4 mM L-Gln, 1.5 g/L sodium bicarbonate and 4.5 g/L glucose supplemented with 100 ug/ml hygromycin and 10% FBS). When confluent, the cells were trypsinized and resuspended in assay medium (0.5% serum-containing DMEM). After 100 ul/well of cells suspension was added to the 96-well-plate (Final cell concentration is 15,000 cells/well), cells were cultured for additional 48 hours before adding the compounds.

Compounds were serially diluted in DMSO and further diluted with assay medium. In an embodiment, 10 nM SAG was added in assay medium as the agonist of Hh signaling. After the compounds and agonist were prepared, carefully remove medium (Aspirate the medium with pipette instead of vacuum, or else the NIH3T3 cells monolayer will be detached). 100 ul of assay medium containing compound or agonist was added to the cell with care. Cell plates were incubated at 37 degree for additional 48 hours.

Figure 10:
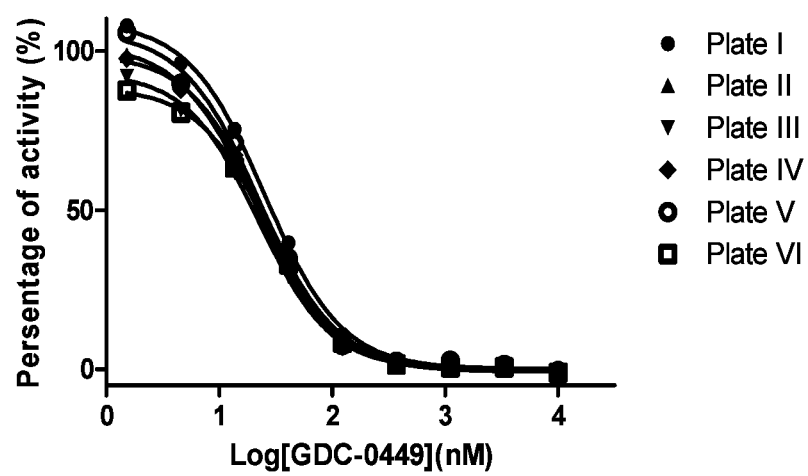
FIG. 10 depicts the IC50 curves of the standard compound A in the primary assay

Following the 48 hours incubation, 40 ul/well of luciferase media (Brigh-Glo, Promega) was added to the cells. The plate was incubated at room temperature for 5 min under gentle shaking. Luminescence signal was measured with plate reader (PHERAstar FS, BMG). The potency of compounds was calculated basing on the inhibition of luminescence signaling. Curves of the IC50 measurement for standard GDC-0449 (vismodegib) when using the primary assay are shown in FIG. 10.

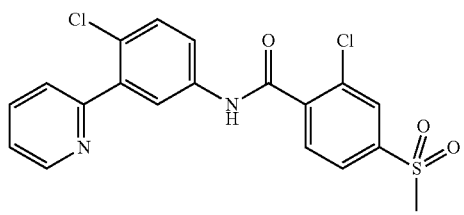 [SMILES: CS(=O)(=O)c1ccc(C(=O)Nc2ccc(Cl)c(-c3ccccn3)c2)c(Cl)c1]

Gdc-0449 (Vismodegib)

The confirmation assay is based on Bodipy-Cyclopamine Binding Assay:

Bodipy-Cyclopamine binding assay is a fluorescence based assay used to analysis the binding of Smo agonists. Hek293-SMO stable clones were established by puromycin (1 ug/ml, Invitrogen) selection after transfection with SMO-HA-pLVX plasmid Hek293-SMO cells were maintained in complete culture medium (DMEM with 4 mM L-Gln, 1.5 g/L sodium bicarbonate and 4.5 g/L glucose supplemented with 100 ug/ml hygromycin and 10% FBS). The expression of SMO was validated with western blot and cell immunofluorescence. Bodipy-Cyclopamine was purchased from Toronto Research Chemicals and dissolved in methanol.

Hek293-SMO cells were plated in 96-well-plate (3340, Corning), the final cell concentration is 15,000 cells/well in 100 ul 1% serum-containing DMEM. The plates were incubated in 37 degree for additional 48 hours.

Hek293-SMO plate were washed with PBS and fixed with 4% paraformaldehyde (PFA)/PBS for 20 min at room temperature. After removing the PFA buffer, the cells were incubated with DAPI/PBS (5 ug/mL) for 10 min and followed by twice wash with PBS. After wash, cells were incubated for 2 h at room temperature in binding buffer (HBSS W/O $Ca^{2+}$ and $Mg^{2+}$) containing 100 nM bodipy-cyclopamine and compounds over a range of concentrations from 0-10 μM for competitive binding. After incubation, the cells were washed twice with the PBS. The fluorescence images were automatically captured and analyzed by a high content fluorescence imaging system (Arrayscan VTI, Thermo). GDC-0449 was used as reference compound to normalize the data. IC50 values were calculated with GraphPad Prism software using the sigmoidal dose-response function. The Ki was calculated following the Cheng-Prusoff equation, as $K_i=IC_{50}/[1+[bodipy-cyclopamine]/K_d)]$. The $K_d$ of bodipy-cyclopamine for WT-Smo is 3.5±0.8 nM.

Figure 11:
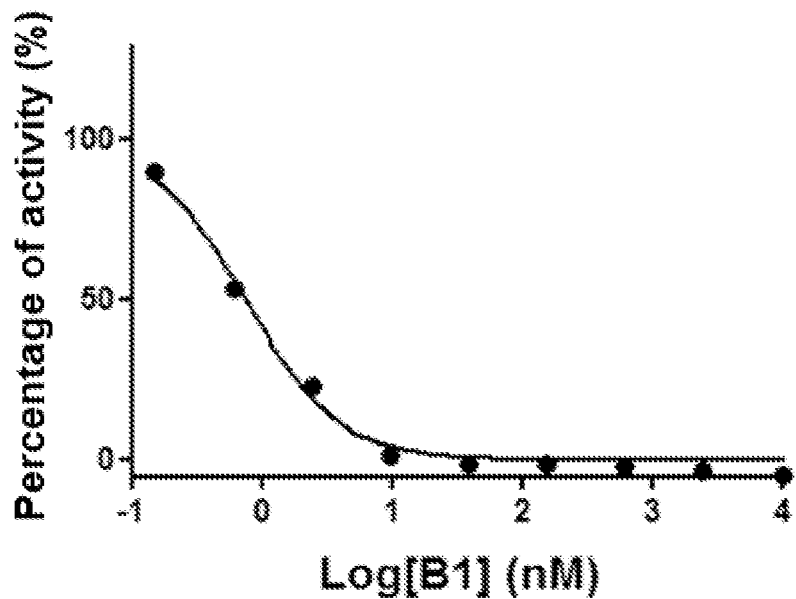
FIG. 11 depicts the IC50 curve of compound B1 in the primary assay.
Figure 12:
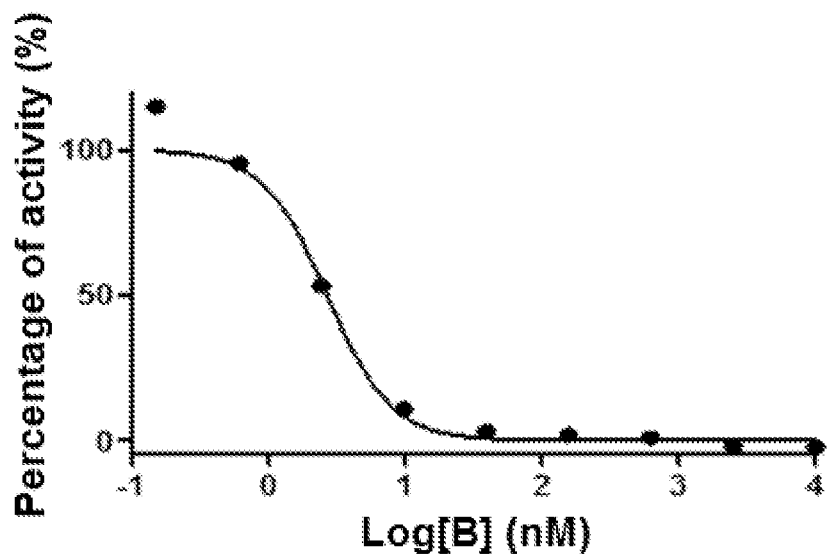
FIG. 12 depicts the IC50 curve of compound B in the primary assay.
Figure 13:
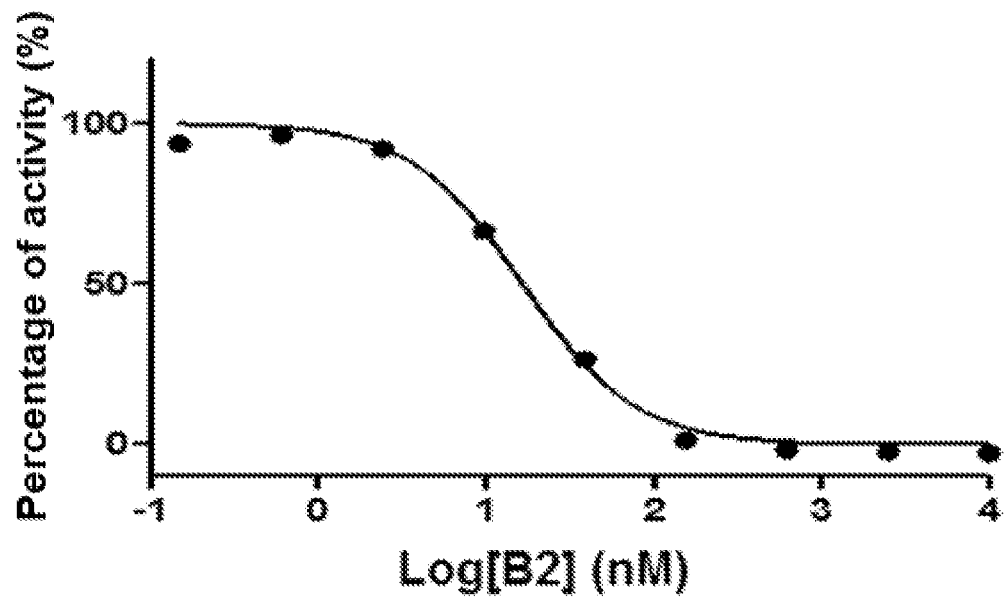
FIG. 13 depicts the IC50 curve of compound B2 in the primary assay.

The above mentioned compounds and several other compounds were tested in the assays described above and the data were summarized in Table 5. The standard compound was Vismodegib and its potency was listed in column 4 as a control. The ratio was the $IC_{50}$ value of Vismodegib over that of the tested compound in the same assay. Some of the tested curves are shown in FIGS. 11-13.

TABLE 5

Test results of selected compounds (B1-B6) of the present invention and other compounds (B-D) in the primary essay.

| Compd. | Structure | SMO $IC_{50}$ (nM) | SMO $IC_{50}$ (nM) (vismodegib) | Ratio |
|---|---|---|---|---|
| B | 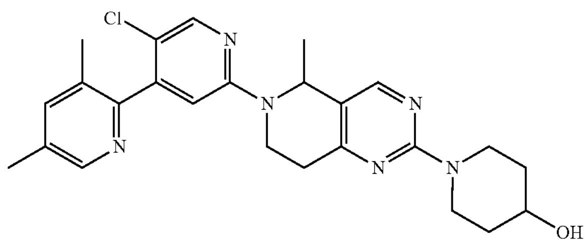 [SMILES: Cc1cnc(-c2cc(N3CCc4nc(N5CCC(O)CC5)ncc4C3C)ncc2Cl)c(C)c1] | 2.7 | 13.4 | 5.0 |
| B1 | 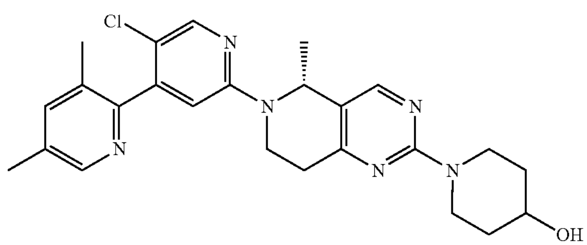 [SMILES: Cc1cnc(-c2cc(N3CCc4nc(N5CCC(O)CC5)ncc4[C@H]3C)ncc2Cl)c(C)c1] | 0.8 | 17.9 | 22.4 |
| B2 | 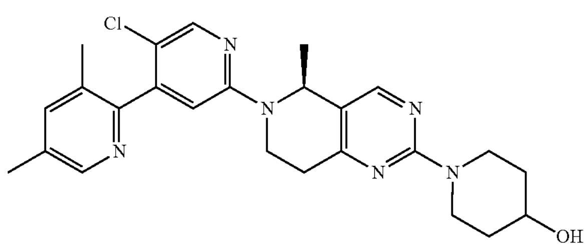 [SMILES: Cc1cnc(-c2cc(N3CCc4nc(N5CCC(O)CC5)ncc4[C@@H]3C)ncc2Cl)c(C)c1] | 17 | 19.3 | 1.1 |
| B3 | 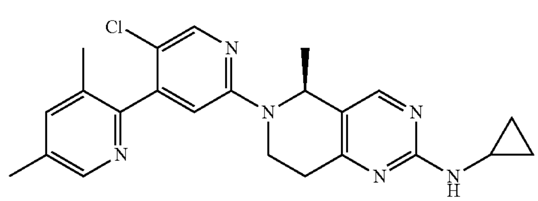 [SMILES: Cc1cnc(-c2cc(N3CCc4nc(NC5CC5)ncc4[C@@H]3C)ncc2Cl)c(C)c1] | 4.0 | 12.4 | 3.1 |

TABLE 5-continued

Test results of selected compounds (B1-B6) of the present invention and other compounds (B-D) in the primary essay.

| Compd. | Structure | SMO IC$_{50}$ (nM) | SMO IC$_{50}$ (nM) (vismodegib) | Ratio |
|---|---|---|---|---|
| B4 | 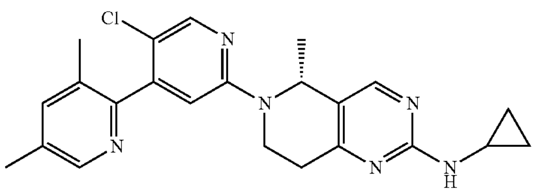 | 2.2 | 17.9 | 8.1 |
| B5 | 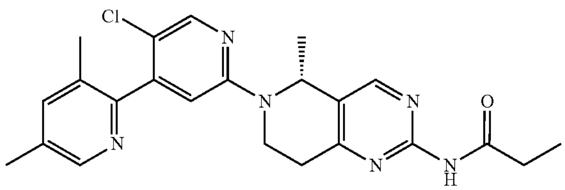 [SMILES: CCC(=O)Nc1ncc2c(n1)CCN(c1cc(-c3ncc(C)cc3C)c(Cl)cn1)[C@@H]2C] | 75 | 26 | 0.35 |
| B6 | 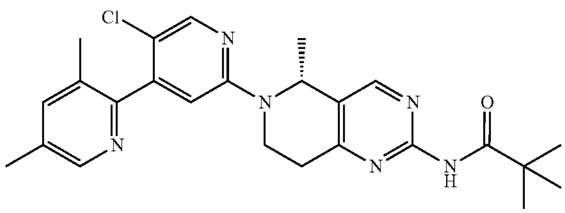 [SMILES: Cc1cnc(-c2cc(N3CCc4nc(NC(=O)C(C)(C)C)ncc4[C@H]3C)ncc2Cl)c(C)c1] | 3.9 | 26 | 6.7 |
| C | 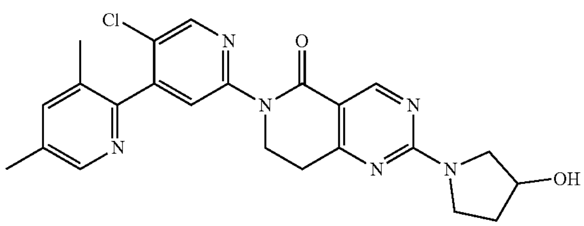 [SMILES: Cc1cnc(-c2cc(N3CCc4nc(N5CCC(O)C5)ncc4C3=O)ncc2Cl)c(C)c1] | 271.7 | 44.6 | 0.16 |
| D | 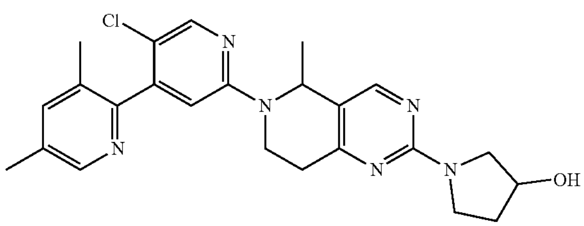 [SMILES: Cc1cnc(-c2cc(N3CCc4nc(N5CCC(O)C5)ncc4C3C)ncc2Cl)c(C)c1] | 4.2 | 13.4 | 3.2 |
| E | 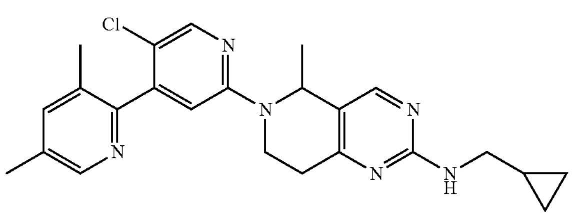 [SMILES: Cc1cnc(-c2cc(N3CCc4nc(NCC5CC5)ncc4C3C)ncc2Cl)c(C)c1] | 7.7 | 13.4 | 1.74 |
| F | 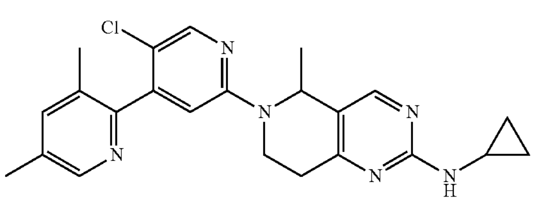 [SMILES: Cc1cnc(-c2cc(N3CCc4nc(NC5CC5)ncc4C3C)ncc2Cl)c(C)c1] | 4.4 | 19.8 | 4.5 |

The invention claimed is:

1. A compound of Formula III:

Formula III or a pharmaceutically acceptable salt, stereoisomer, or solvate thereof, wherein $R_2$ and $R'_2$ are independently H, $C_{1-3}$ alkyl, $CD_3$, or $CF_3$, with the proviso that at least one of $R_2$ and $R'_2$ is not H;

$R_1$ is —NRxRy, wherein Rx and Ry are independently H, alkyl, cycloalkyl, alkylcycloalkyl, C(O)R", or —NRxRy together to form wherein $W_{10}$ is H or D;

R" is $C_{1-5}$ alkyl;

$W_1$, $W_2$, $W_3$, $W_4$, $W_5$, $W_6$, $W_7$, $W_8$ and $W_9$ are independently H or D; and A is N or CH.

2. The compound of claim 1, wherein $R_1$ is:

and $W_{10}$ is H or D.

3. The compound of claim 2, wherein $R'_2$ is H; and $R_2$ is $C_{1-3}$ alkyl or $CF_3$.

4. The compound of claim 1, wherein $R'_2$ is H; and $R_2$ is $CH_3$ or $CD_3$.

5. The compound of claim 4, wherein $R_1$ is and $W_{10}$ is H or D.

6. The compound of claim 5, wherein A is N.

7. The compound of claim 1, wherein the compound is according to Formula IV:

Formula IV or a pharmaceutically acceptable salt, or solvate thereof, wherein $R_2$ is $C_{1-3}$ alkyl, $CD_3$, or $CF_3$;

$R_1$ is —NRxRy, wherein Rx and Ry are independently H, alkyl, cycloalkyl, alkylcycloalkyl, C(O)R", or —NRxRy together to form wherein $W_{10}$ is H or D;

R" is $C_{1-5}$ alkyl; and $W_1$, $W_2$, $W_3$, $W_4$, $W_5$, $W_6$, $W_7$, $W_8$ and $W_9$ are independently H or D.

8. The compound of claim 7, wherein $R_1$ is

-continued

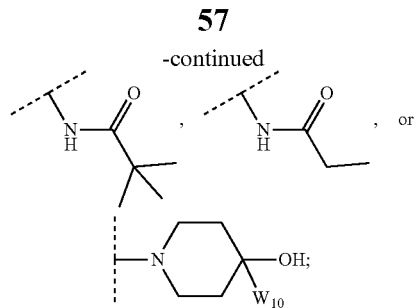

and W$_{10}$ is H or D.

9. The compound of claim 7, wherein R$_2$ is C$_{1-3}$ alkyl or CF$_3$.

10. The compound of claim 7, wherein R$_2$ is CH$_3$ or CD$_3$.

11. The compound of claim 10, wherein R$_1$ is

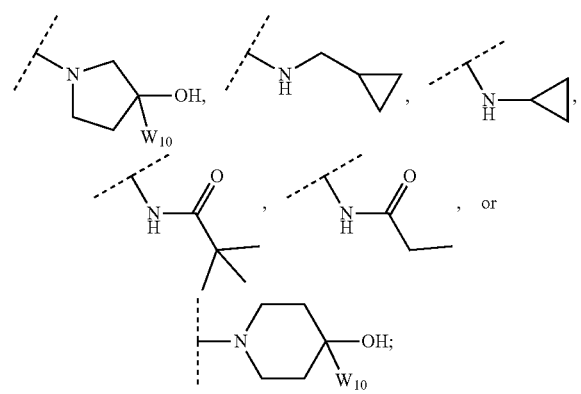

and W$_{10}$ is H or D.

12. The compound of claim 7 wherein the compound is selected from the group consisting of:

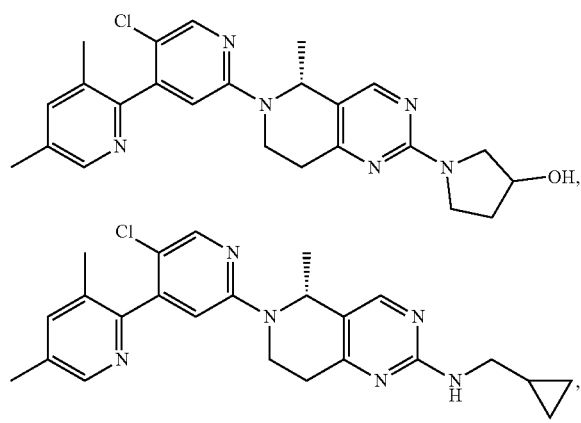

-continued

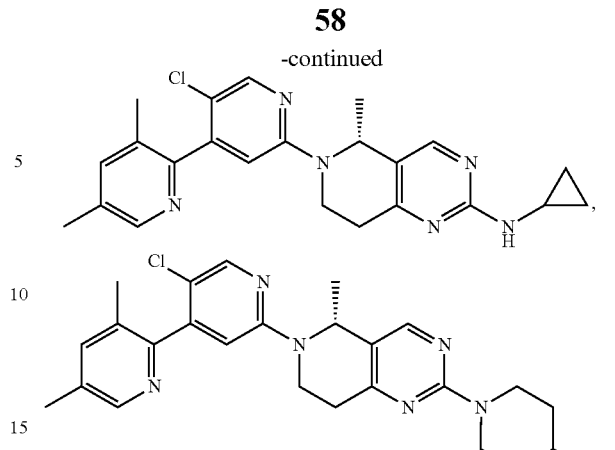

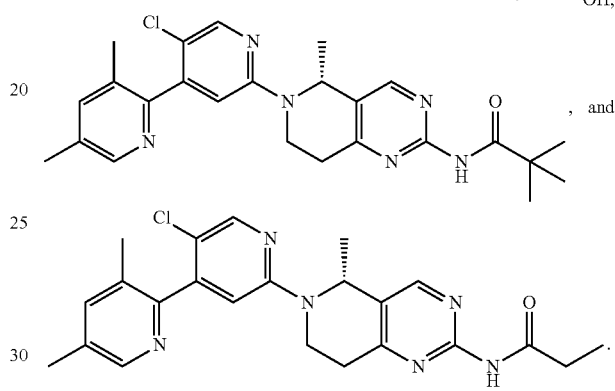

13. A pharmaceutical composition comprising a compound of claim 1 and a pharmaceutically acceptable carrier.

14. A method for inhibiting smoothened transmembrane protein (SMO) in a patient diagnosed with a hyperproliferative disorder, comprising administering to the patient a composition comprising a SMO inhibitor in an effective amount to reduce the activation of the hedgehog-patched pathway in a cell of the patient, wherein the SMO inhibitor is a compound of claim 1.

15. The method of claim 14, wherein the hyperproliferative disorder is liver cancer, lung cancer, rectal cancer, cervical cancer, pancreatic cancer, breast cancer, gastric cancer, oral cancer, esophageal cancer, nasopharyngeal carcinoma, skin cancer, bone cancer, brain cancer, kidney cancer, blood cancer, or a combination thereof.

16. The method of claim 14, wherein the composition further comprises at least two pharmaceutically acceptable salts of the compound.

17. The method of claim 16, wherein the composition further comprises one or more compounds selected from the group consisted of cisplatin, paclitaxel, camptothecin, trastuzumab, imatinib, gefitinib, erlotinib and lapatinib.

18. The method of claim 14, wherein the composition further comprises one or more compounds selected from the group consisted of cisplatin, paclitaxel, camptothecin, trastuzumab, imatinib, gefitinib, erlotinib and lapatinib.

* * * * *

UNITED STATES PATENT AND TRADEMARK OFFICE
CERTIFICATE OF CORRECTION

| | | |
|---|---|---|
| PATENT NO. | : 10,919,889 B2 | Page 1 of 1 |
| APPLICATION NO. | : 16/313090 | |
| DATED | : February 16, 2021 | |
| INVENTOR(S) | : Xiaohu Zhang | |

It is certified that error appears in the above-identified patent and that said Letters Patent is hereby corrected as shown below:

On the Title Page

Item (71) Applicant, delete the entirety of the item and replace with --Suzhou Kintor Pharmaceuticals, Inc., Suzhou, Jiangsu (CN)-- therefor.

Item (72) Inventor, delete the entirety of the item and replace with --Xiaohu Zhang, Suzhou, Jiangsu (CN)-- therefor.

Item (73) Assignee, delete the entirety of the item and replace with --Suzhou Kintor Pharmaceuticals, Inc., Suzhou, Jiangsu (CN)-- therefor.

Signed and Sealed this
Eighteenth Day of May, 2021

Drew Hirshfeld
*Performing the Functions and Duties of the
Under Secretary of Commerce for Intellectual Property and
Director of the United States Patent and Trademark Office*